US011083501B2

(12) United States Patent
Grizzard et al.

(10) Patent No.: US 11,083,501 B2
(45) Date of Patent: Aug. 10, 2021

(54) SURGICAL SYSTEM AND METHOD

(71) Applicant: Warsaw Orthopedic, Inc., Warsaw, IN (US)

(72) Inventors: Mark Grizzard, Munford, TN (US); Robert Loke, Memphis, TN (US); Dustin Bobbitt, Olive Branch, MS (US); John Elliott, Atoka, TN (US); Julien J. Prevost, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 294 days.

(21) Appl. No.: 16/393,822

(22) Filed: Apr. 24, 2019

(65) Prior Publication Data
US 2020/0337744 A1    Oct. 29, 2020

(51) Int. Cl.
| | | |
|---|---|---|
| *A61B 17/70* | (2006.01) | |
| *A61B 17/88* | (2006.01) | |
| *A61B 17/00* | (2006.01) | |

(52) U.S. Cl.
CPC ...... *A61B 17/7098* (2013.01); *A61B 17/7032* (2013.01); *A61B 17/7035* (2013.01); *A61B 17/8805* (2013.01); *A61B 2017/00004* (2013.01); *A61B 2017/0088* (2013.01); *A61B 2017/00867* (2013.01); *A61B 2017/00933* (2013.01)

(58) Field of Classification Search
CPC .......... A61B 17/7098; A61B 17/8805
See application file for complete search history.

(56) References Cited

U.S. PATENT DOCUMENTS

| | | |
|---|---|---|
| 2,691,979 A | 10/1954 | Watson |
| 5,390,383 A | 2/1995 | Carn |
| 6,021,343 A | 2/2000 | Foley |
| 7,189,214 B1 | 3/2007 | Saunders |
| 7,234,180 B2 | 6/2007 | Horten et al. |
| 7,290,302 B2 | 11/2007 | Sharps |
| 7,496,980 B2 | 3/2009 | Sharps |
| 8,747,411 B2 * | 6/2014 | Mitchell ............ A61B 17/7098 606/104 |
| 8,784,431 B1 | 7/2014 | Harder |
| 9,192,415 B1 | 11/2015 | Arnold |
| 2003/0023243 A1 | 1/2003 | Biedermann |
| 2005/0228400 A1 | 10/2005 | Chao |
| 2007/0043378 A1 | 2/2007 | Kumar |

(Continued)

FOREIGN PATENT DOCUMENTS

| | | |
|---|---|---|
| WO | 2007058673 A1 | 5/2007 |
| WO | 2017031225 A1 | 2/2017 |

*Primary Examiner* — Andrew Yang
(74) *Attorney, Agent, or Firm* — Sorell, Lenna & Schmidt, LLP

(57) ABSTRACT

A surgical system includes a sleeve defining a passageway. An adapter is removably coupled to the sleeve. The adapter defines a channel. A delivery device includes a distal end positioned in a channel of the adapter. A bone fastener includes a head and a shank defining a cannula. A distal portion of the adapter is positioned in the shank such that the channel is in communication with a cannula of the shank. A plunger is movably disposed in a lumen of the delivery device. The plunger is configured to move a material through the lumen and the channel and into the cannula. Methods and kits are disclosed.

20 Claims, 24 Drawing Sheets

(56) References Cited

U.S. PATENT DOCUMENTS

| | | |
|---|---|---|
| 2008/0045970 A1 | 2/2008 | Saidha |
| 2008/0134434 A1 | 6/2008 | Celauro |
| 2010/0037397 A1 | 2/2010 | Wood |
| 2010/0249798 A1 | 9/2010 | Sournac |
| 2011/0046683 A1 | 2/2011 | Biedermann |
| 2012/0144689 A1 | 6/2012 | Skripps et al. |
| 2013/0103039 A1 | 4/2013 | Hopkins |
| 2013/0111666 A1 | 5/2013 | Jackson |
| 2013/0261609 A1 | 10/2013 | Dicorleto |
| 2013/0282019 A1 | 10/2013 | Bouliane |
| 2013/0345718 A1 | 12/2013 | Crawford |
| 2014/0109316 A1 | 1/2014 | Jackson et al. |
| 2014/0100616 A1 | 4/2014 | Shipp |
| 2014/0107708 A1 | 4/2014 | Biedermann |
| 2014/0371756 A1 | 12/2014 | Marigowda |
| 2015/0105831 A1 | 4/2015 | Yim |
| 2015/0105833 A1 | 4/2015 | Simpson |
| 2015/0201985 A1 | 7/2015 | Rampersaud |
| 2015/0201987 A1 | 7/2015 | Lemoine |
| 2015/0250512 A1 | 9/2015 | Poker |
| 2015/0282855 A1 | 10/2015 | Bess |
| 2015/0359572 A1 | 12/2015 | Reimels |
| 2016/0030100 A1 | 2/2016 | Divincenzo |
| 2016/0047394 A1 | 2/2016 | Lee |
| 2016/0262809 A1 | 9/2016 | May |
| 2016/0296266 A1 | 10/2016 | Chandanson |
| 2017/0049651 A1 | 2/2017 | Lim et al. |
| 2017/0049653 A1 | 2/2017 | Lim et al. |
| 2017/0079696 A1 | 3/2017 | Walker |
| 2017/0333093 A1 | 11/2017 | Krier |
| 2018/0014863 A1 | 1/2018 | Biester |
| 2018/0042650 A1 | 2/2018 | Gao |
| 2018/0064497 A1 | 3/2018 | Hussain |
| 2018/0147018 A1 | 5/2018 | Crawford |
| 2018/0153591 A1 | 6/2018 | Schafer |
| 2018/0177536 A1 | 6/2018 | Divincenzo |
| 2018/0214190 A1 | 8/2018 | Erramilli |

* cited by examiner

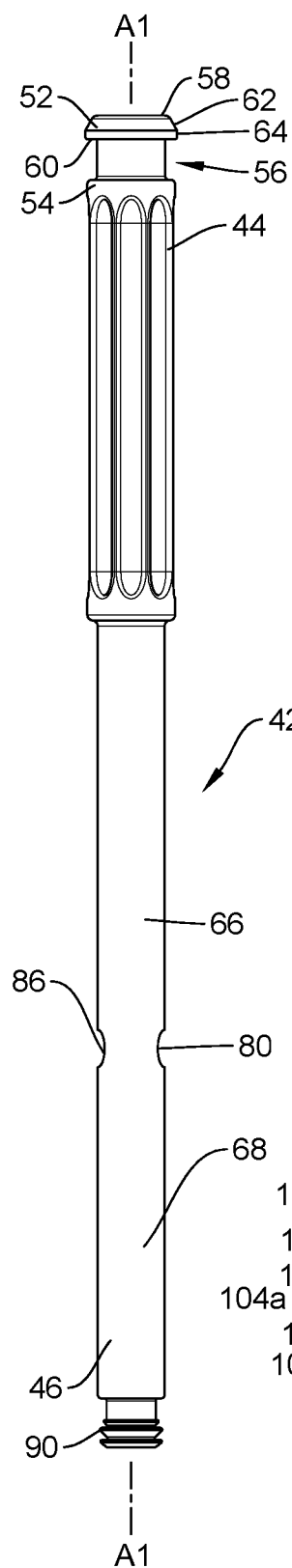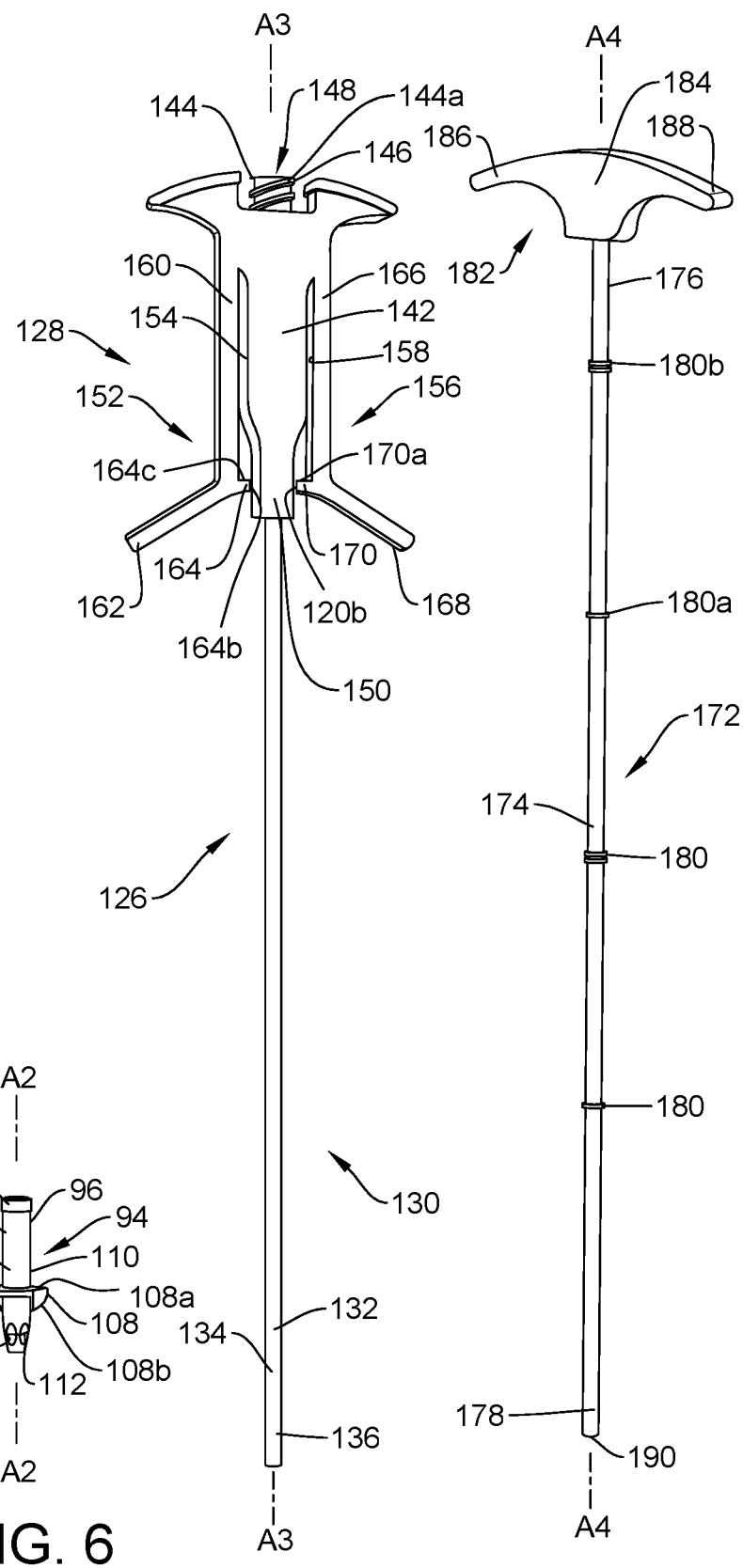
FIG. 5  FIG. 6  FIG. 7  FIG. 8

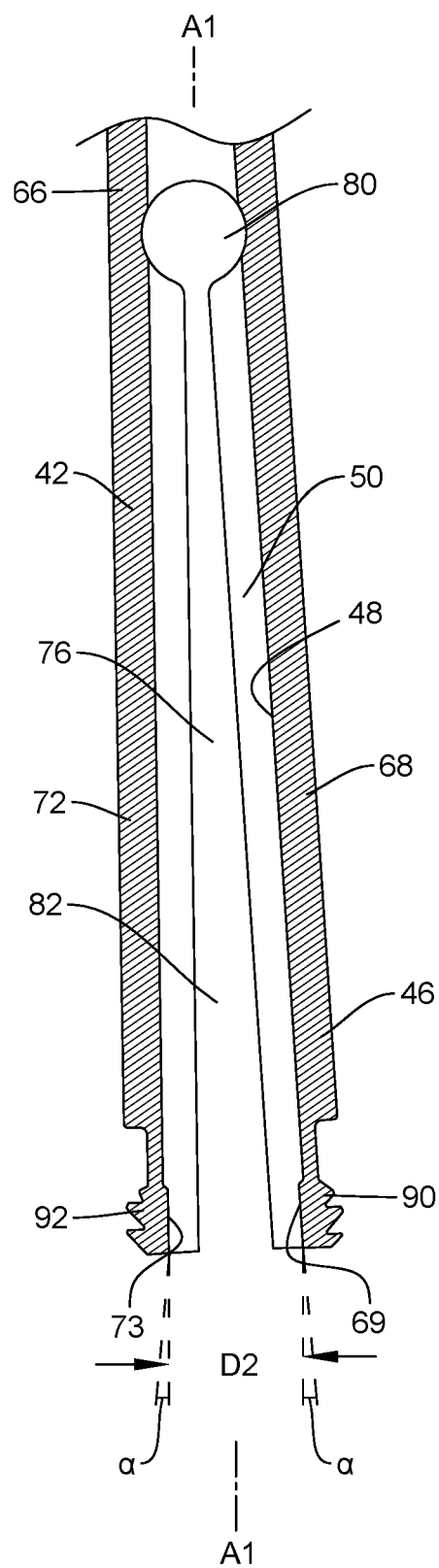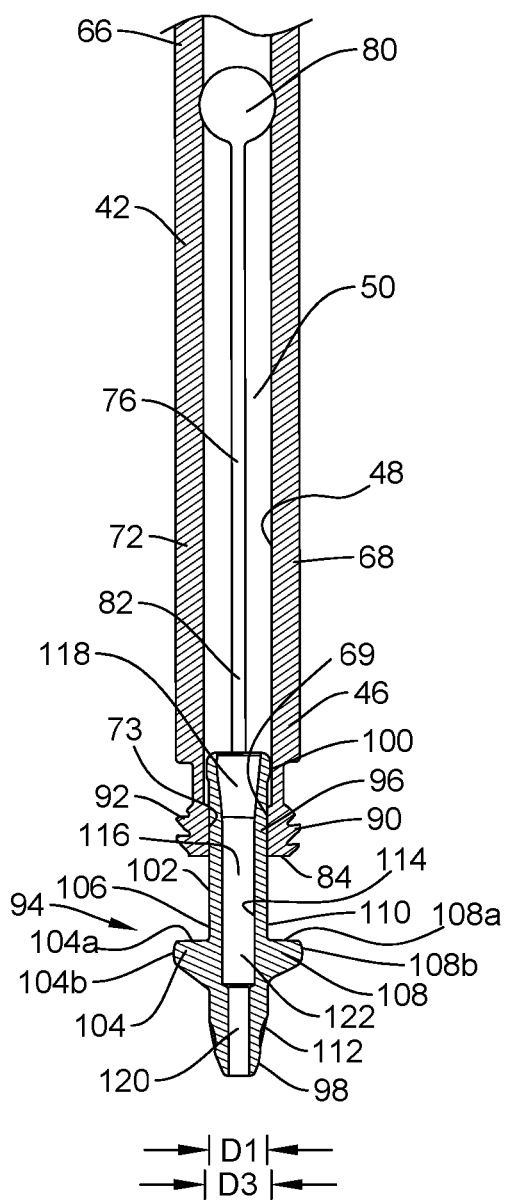
FIG. 11B
FIG. 11C

SURGICAL SYSTEM AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the bone fasteners to the exterior of two or more vertebral members. A surgeon may stabilize the vertebra by using a driver to insert the bone fasteners into the damaged vertebral body and attach the fasteners to one or more rods to help support and stabilize the damaged vertebra.

It is sometimes difficult for the surgeon to achieve the required support and stabilization for the damaged vertebral body because the threads of the bone fasteners do not properly engage the vertebral bone. Therefore, the surgeon may use a bone filler device in connection with a driver to deliver an adhesive material or cement material in and/or around at least one of the bone fasteners to further bond at least one of the fasteners with bone. However, the volume of cement that can be dispensed with conventional bone filler devices does not match spinal augmentation guidance. As such, more than one bone filler device is often required to deliver a volume of cement sufficient to bond a single bone fastener with bone, or to deliver a second amount of cement after the delivery of a first amount of cement. Furthermore, conventional drivers, which are heavy, monolithic devices, must be discarded after a single use due to hardened cement within the driver. This disclosure describes an improvement over these prior technologies.

SUMMARY

In one embodiment, a surgical system is provided. The surgical system includes a sleeve comprising a proximal end including a first mating element and a distal end including a second mating element. The sleeve defines a passageway. An adapter is removably coupled to the sleeve. The adapter defines a channel. The adapter includes a distal portion and a proximal portion positioned in the passageway. A delivery device comprises a handle and a shaft. A distal end of the shaft is positioned in the channel. The handle includes a third mating element configured to engage the first mating element to connect the delivery device to the sleeve. The shaft defines a lumen in communication with the channel. A bone fastener includes a head and a shank defining a cannula. The head comprises a fourth mating element configured to engage the second mating element to connect the bone fastener to the sleeve. The distal portion is positioned in the shank such that the channel is in communication with the cannula. A plunger is movably disposed in the lumen and configured to move a material through the lumen and the channel and into the cannula. In some embodiments, methods and kits are disclosed.

In one embodiment, a surgical method is disclosed. The surgical method comprises: connecting an adapter with a sleeve such that a channel of the adapter is in communication with a passageway of the sleeve; engaging a first mating element of the sleeve with a second mating element of a bone fastener to connect the bone fastener with the sleeve such that the channel is in communication with a cannula of the bone fastener; engaging a third mating element of the sleeve with a fourth mating element of a delivery device to connect the delivery device with the sleeve such that a lumen of the delivery device is in communication with the channel; inserting a material into the lumen; and inserting a plunger into the lumen such that the plunger moves the material through the lumen and the channel and into the cannula.

In one embodiment, a surgical kit is provided. The surgical kit comprises bone cement. The surgical kit includes a sleeve comprising a proximal end including a first mating element and a distal end including a second mating element. The sleeve defines a passageway. The surgical kit includes a plurality of adapters. The adapters are each configured to be removably coupled to the sleeve. The adapters each define a channel. The adapters each include a distal portion and a proximal portion configured to be positioned in the passageway. The surgical kit includes a delivery device comprising a handle and a shaft. A distal end of the shaft is configured to be positioned in a respective one of the channels. The handle includes a third mating element configured to engage the first mating element to connect the delivery device to the sleeve. The shaft defines a lumen configured to be in communication with a respective one of the channels. The surgical kit includes a plurality of bone fasteners. The bone fasteners each include a head and a shank defining a cannula. The heads each comprise a fourth mating element configured to engage the second mating element to connect the bone fasteners to the sleeve. A respective one of the distal portions is configured to be positioned in a respective one of the shanks such that a respective one of the channels is in communication with a respective one of the cannulas. The surgical kit includes a plunger configured to be movably disposed in the lumen and to move the bone cement through the lumen and a respective one of the channels and into a respective one of the cannulas.

BRIEF DESCRIPTION OF THE DRAWINGS

The present disclosure will become more readily apparent from the specific description accompanied by the following drawings, in which:

FIG. 5 is a side view of a first component of the embodiment of the surgical system shown in FIG. 1;

FIG. 6 is a side view of a second component of the embodiment of the surgical system shown in FIG. 1;

FIG. 7 is a side view of a third component of the embodiment of the surgical system shown in FIG. 1;

FIG. 8 is a side view of a fourth component of the embodiment of the surgical system shown in FIG. 1;

FIG. 11B is a side, cross-sectional view of the first component of the embodiment of the surgical system shown in FIG. 1, with the first component in an expanded configuration;

FIG. 11C is a side, cross-sectional view of the first and second components of the embodiment of the surgical system shown in FIG. 1, with the first component in the non-expanded configuration;

DETAILED DESCRIPTION

Figure 1:
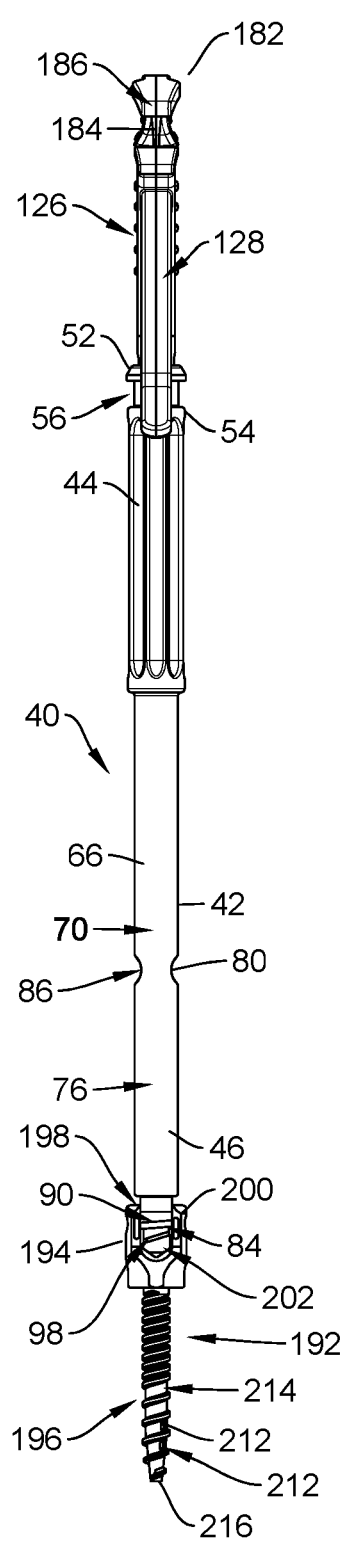
FIG. 1 is a first side view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system, a surgical method and a surgical kit. In some embodiments, the systems, methods and kits of the present disclosure comprise medical devices including surgical instruments and implants that are employed with a surgical treatment, as described herein, for example, with a cervical, thoracic, lumbar and/or sacral region of a spine.

A fenestrated screw is sometimes used to deliver a material, such as, for example, bone cement to a selected area to securely implant the screw with bone. With conventional fenestrated screw instrumentation solutions, a driver is attached to a shank of the screw and the driver is rotated to drive the shank into bone. Bone cement is injected into the driver. A plunger or hydraulic pressure then pushes the bone cement through the driver and a cannula of the shank such that the bone cement exits the screw through fenestrations in the shank. However, conventional fenestrated screw instrumentation solutions are not optimized for spinal needs. For example, the volume of bone cement available with conventional fenestrated screw instrumentation solutions does not match spinal augmentation guidance. Indeed, since conventional fenestrated screw instrumentation solutions were developed primarily for kyphoplasty procedures, conventional fenestrated screw instrumentation solutions were adapted to hold only about 1.5 cubic centimeters (cc) of bone cement, which is insufficient for lumbar spine screw cement augmentation procedures, which require between about 1.5 cc and about 2.0 cc of bone cement. The drivers of conventional fenestrated screw instrumentation solutions are not reusable, due to the potential risk of infection caused if tissue from prior procedures were trapped in hardened cement within the driver. As such, a surgeon would need to use more than one plunger of a conventional fenestrated screw instrumentation solution to inject a sufficient amount of bone cement through a single screw. That is, after the bone cement from a first plunger of a conventional fenestrated screw instrumentation solution was delivered into a screw, the first plunger of a conventional fenestrated screw instrumentation solution would need to be discarded. A second plunger of a conventional fenestrated screw instrumentation solution would then need to be attached to the driver to deliver an additional amount of bone cement through the screw. Accordingly, the surgical system disclosed herein is configured to the required amount of bone cement to match spinal augmentation guidance, as discussed herein.

Conventional fenestrated screw instrumentation solutions also tend to waste a relatively large amount of bone cement. For example, while conventional fenestrated screw instrumentation solutions can be adapted to hold about 1.5 cc of bone cement, about 0.5 cc of bone cement adheres to an interior of the driver. As such, conventional fenestrated screw instrumentation solutions are only capable of delivering about 1.0 cc of to the screw. Therefore, a surgeon using of a conventional fenestrated screw instrumentation solution will need to use more than one plungers or BFDs to inject a sufficient amount of bone cement through a single screw. This is both costly and time consuming. Accordingly, the surgical system disclosed herein includes a small, disposable tip that attaches to a sleeve of a driver and wastes only about 0.1 cc of bone cement. In one embodiment, the surgical system of the present disclosure is adapted to hold approximately 1.9 cc of bone cement so about 1.8 cc of bone cement can be delivered to a screw, which is the precise amount recommended for lumbar spine screw cement augmentation procedures. It is envisioned that the surgical system of the present disclosure can be adapted to dispense the required amount of bone cement to match spinal augmentation guidance. For example, in augmentation procedures for the thoracic spine, for which about 0.8 cc of bone cement is recommended, the surgical system can be adapted to hold about 0.9 cc of bone cement so that about 0.8 of bone cement will be delivered to the screw even if about 0.1 cc is lost in the reusable tip. In some embodiments, the adaption of the surgical system is facilitated by the use of laser mark graduations on a plunger of the surgical system.

As noted above, the drivers of conventional fenestrated screw instrumentation solutions must be discarded after being used to deliver bone cement to a screw due to bone cement hardening within the driver. Indeed, because the hardened bone cement can include tissue from prior surgeries, it could be a potential source of infection if reused. Since the drivers are long pieces of precision manufactured stainless steel, both the capital cost and perception of disposing the drivers after only one use can be significant. Accordingly, the surgical system disclosed herein includes a cement delivery guide with a sleeve and a removable tip that attaches to the sleeve. A nozzle of the bone filler device fits within a proximal end of the tip to allow bone cement to flow only through the disposable tip and directly into the screw shank. Since the bone cement does not contact the interior of the sleeve, only the tip needs to be discarded and the sleeve can be reused to minimize the amount of waste.

In some embodiments, the surgical system of the present disclosure includes two main components. The first component is a bone filler device. The bone filler device is used to contain bone cement that is then delivered through fenestrated implants by way of connection to a cement delivery guide. A plunger with graduations is aligned to spinal recommendations. For example, the plunger has graduations that allow a surgeon to know how much bone cement has been dispensed from the bone filler device by aligning a respective one of the graduations with a portion of the bone filler device and/or a portion of the cement delivery guide.

The second component is the cement delivery guide. The cement delivery guide includes a reusable sleeve and a disposable alignment tip. The sleeve includes a proximal undercut for connection and retention with the bone filler device. The sleeve further includes a spring tab and thread for connection and retention with the reusable tip. In some embodiments, the sleeve includes a proper assembly indicator line that aligns with a line on an extender when a cement delivery guide is properly assembled with the extender. In some embodiments, the sleeve can be connected with the bone filler device and/or the reusable tip by threads, snap rings, spring tabs, mutual grooves, screws, adhesive, nails, barbs, raised elements, spikes, clips, snaps, friction fittings, compressive fittings, expanding rivets, staples, fixation plates, key/keyslot, tongue in groove, dovetail, magnetic connection and/or posts. In one embodiment, the reusable tip includes a spring tab and thread for connection and retention with the sleeve.

In some embodiments, the surgical system of the present disclosure includes connection features to ensure a seal, such as, for example, a flush seal between the bone filler device and a fenestrated screw. For example, in some embodiments, the removable tip and sleeve are connected with the fenestrated screw. The tip fits within a saddle of a sagittal adjusting screw or within the crown of a multi-axial screw to create a flush seal. The sleeve is threaded into a head of the screw, which puts tension on the tip and ensures a good seal. The bone filler device is then attached to a proximal end of the sleeve and a nozzle of the bone filler device fits within a proximal end of the tip to allow bone cement to flow only through the disposable tip and directly into the screw shank. In some embodiments, the tip is tapered to allow clearance between the saddle and the tip and to help align the saddle into a coaxial position to ensure that the tip seats into the shank correctly.

In some embodiments, the sleeve includes a split tube and the removable tip includes a spherical feature that is pressed into a distal end of the split tube. As the spherical feature is pressed into a distal end of the split tube, the spherical component forces the split tube apart until the inner diameter of the sleeve expands to be greater than the outer diameter of the spherical feature to capture the tip.

In some embodiments, the removable tip includes a body and opposite flanges that extend from the body. The flanges each have a helical configuration to ensure proper orientation of the tip when the tip is connected with the screw. Indeed, if the flanges were straight, it is possible for the tip to catch 90 degrees opposed to its intended orientation. The helical configuration of the flanges helps reorient the tip during insertion of the tip into the screw by converting the downward force into a twist.

In some embodiments, the surgical system of the present disclosure includes at least two types of removable tips. For example, the surgical system can include a tall tip and a short tip. The tall tip can be used in minimally invasive procedures and allows threads at a distal end of the sleeve to engage at the top of the extended height of the screw head. The short tip can be used for a normal height implant. In some embodiments, the tall tip and the short tip can be interchangeably used with a single sleeve. In some embodiments, the surgical system of the present disclosure includes at least two types of sleeves and only one tip of removable tip.

In some embodiments, the surgical system of the present disclosure may be employed to treat spinal disorders such as, for example, degenerative disc disease, disc herniation, osteoporosis, spondylolisthesis, stenosis, scoliosis, kyphosis, and other curvature abnormalities, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system and related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-38, there are illustrated components of a delivery system, such as, for example, a surgical system 40.

The components of surgical system 40 can be fabricated from biologically acceptable materials suitable for medical applications, including metals, synthetic polymers, ceramics and bone material and/or their composites. For example, the components of surgical system 40, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 40 may have material composites, including the above materials, to achieve various desired characteristics such as strength, rigidity, elasticity, compliance, biomechanical performance, durability and radiolucency or imaging preference. The components of surgical system 40, individually or collectively, may also be fabricated from a heterogeneous material such as a combination of two or more of the above-described materials. The components of surgical system 40 may be monolithically formed, integrally connected or include fastening elements and/or instruments, as described herein.

Surgical system 40 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Surgical system 40 includes a cement delivery guide, such as, for example, a sleeve 42 that extends along a longitudinal axis A1 between a proximal end 44 and an opposite distal end 46. Sleeve 42 includes an inner surface 48 that defines a passageway 50. In some embodiments, passageway 50 is coaxial with axis A1 and extends the entire length of sleeve 42. That is, passageway 50 extends between and through opposite end surfaces of ends 44, 46 such that a component of system 40 can be inserted through the end surface of end 44 and into passageway 50 and a component of system 40 can be inserted through the end surface of end 46 and into passageway 50. In some embodiments, passageway 50 has a circular diameter. In some embodiments, passageway 50 has a uniform diameter along the entire length of sleeve 42. In some embodiments, passageway 50 may be disposed at alternate orientations, relative to axis A1, such as, for example, transverse, perpendicular and/or other angular orientations such as acute or obtuse, co-axial and/or may be offset or staggered. In some embodiments, passageway 50 may have various cross section configurations, such as, for example, oval, oblong, triangular, rectangular, square, polygonal, irregular, uniform, non-uniform, variable, tubular and/or tapered. In some embodiments, sleeve 42 is configured to be reused and is made from a metal material, such as, for example, stainless steel to provide strength and rigidity to sleeve 42. However, it is envisioned that sleeve 42 can also be made from any of the other materials discussed herein, such as, for example, stainless steel alloys, commercially pure titanium, titanium alloys, Grade 5 titanium, cobalt-chrome alloys.

Figure 17:
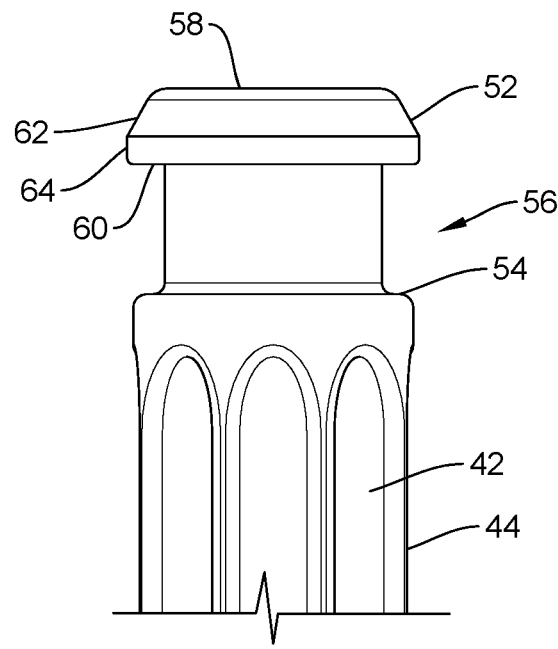
FIG. 17 is a side, breakaway view of the first component of the embodiment of the surgical system shown in FIG. 1.

End 44 includes a mating element, such as, for example, a flange 52 configured to connect a component of system 40, such as, for example, a delivery device 126 with sleeve 42, as discussed herein. Flange 52 is spaced apart from a flange 54 by an undercut, such as, for example, a recess 56. Flange 52 includes opposite surfaces 58, 60 that each extend perpendicular to axis A1 and surfaces 62, 64 that are each positioned between surfaces 58, 60, as best shown in FIG. 17. Surface 58 defines the end surface of end 44. Surface 62 extends transverse to axis A1 and surface 64 extends parallel to axis A1. In some embodiments, surface 58, surface 60, surface 62 and/or surface 64 may be disposed at alternate orientations, relative to longitudinal axis A1, such as, for example, parallel, transverse, perpendicular and/or other angular orientations such as acute or obtuse and/or may be offset or staggered.

Figure 2:
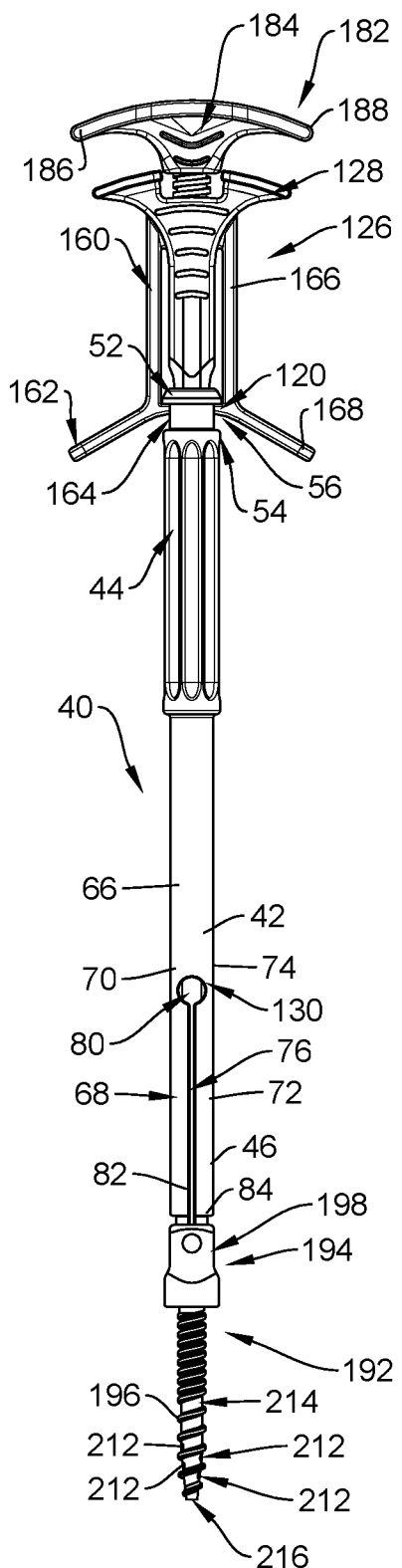
FIG. 2 is a second side view of components of the embodiment of the surgical system shown in FIG. 1.
Figure 3:
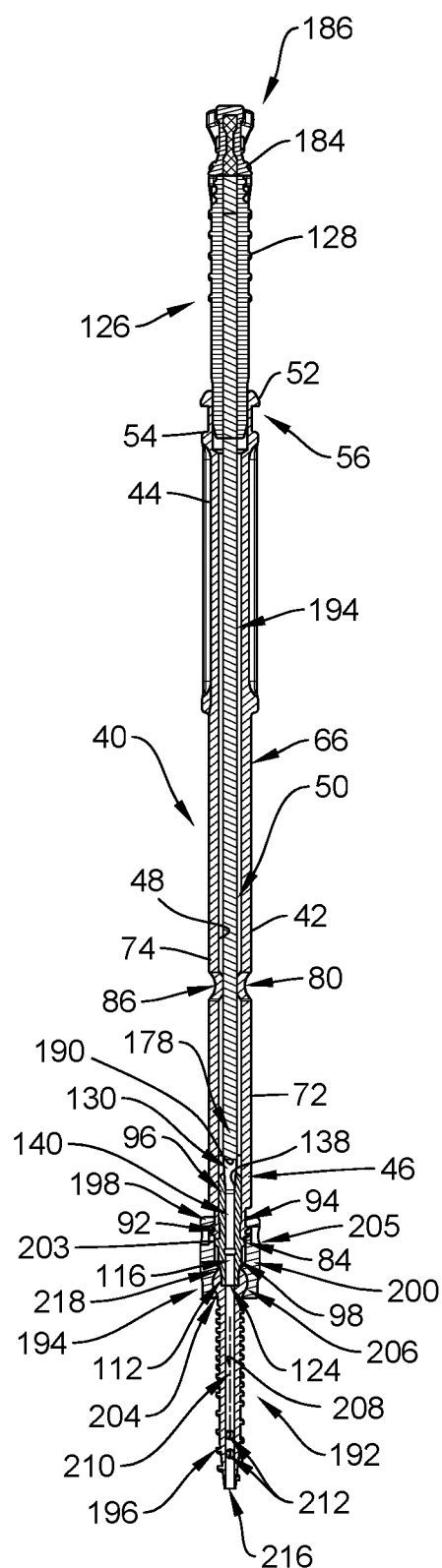
FIG. 3 is a first side, cross-sectional view of components of the embodiment of the surgical system shown in FIG. 1.
Figure 10:
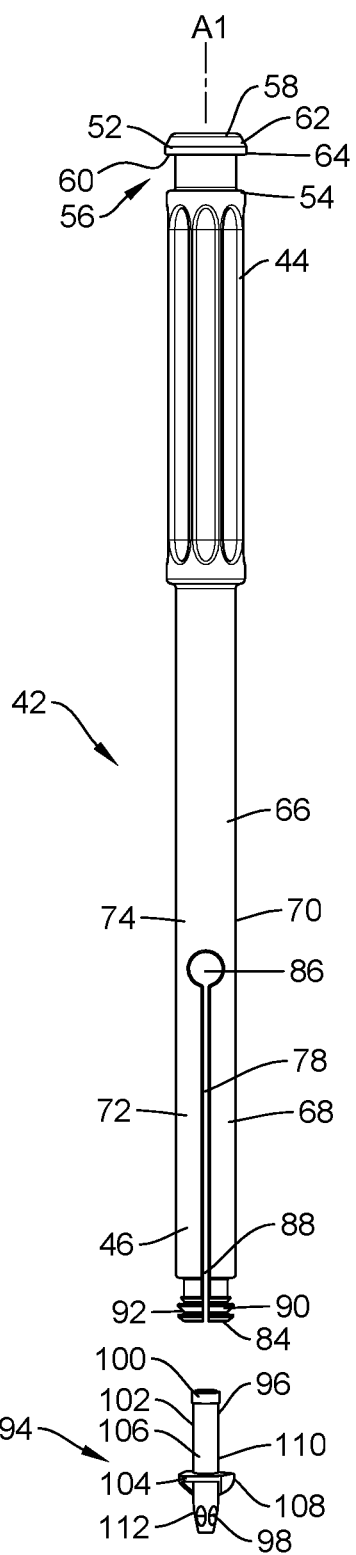
FIG. 10 is a side view of the first and second components of the embodiment of the surgical system shown in FIG. 1, with parts separated.

Sleeve 42 includes a body 66. End 46 includes a leg 68 extending from a side 70 of body 66 and a leg 72 extending from a side 74 of body 66 such that leg 72 faces leg 68. Legs 68, 72 are separated by a gap 76 and a gap 78. Gap 76 includes a substantially circular proximal portion 80 and a linear distal portion 82 that extends through an end surface 84 of end 46, as shown in FIG. 2, for example. Gap 78 is similar to gap 76 and includes a substantially circular proximal portion 86 and a linear distal portion 88 that extends through end surface 84, as shown in FIG. 10, for example. Portion 80 is aligned with portion 86 such that portions 80, 86 extend through a thickness of sleeve 42. Portion 82 is aligned with portion 88 such that portions 82, 88 extend through the thickness of sleeve 42. In some embodiments, portion 80 and/or portion 86 is variously shaped, such as, for example, oval, oblong, triangular, square, polygonal, irregular, uniform, non-uniform, offset, staggered, undulating, arcuate, variable and/or tapered. In some embodiments, portion 82 and/or portion 88 may be disposed at alternate orientations, relative to axis A1, such as, for example, transverse, perpendicular and/or other angular orientations such as acute or obtuse, co-axial and/or may be offset or staggered.

Figure 11A:
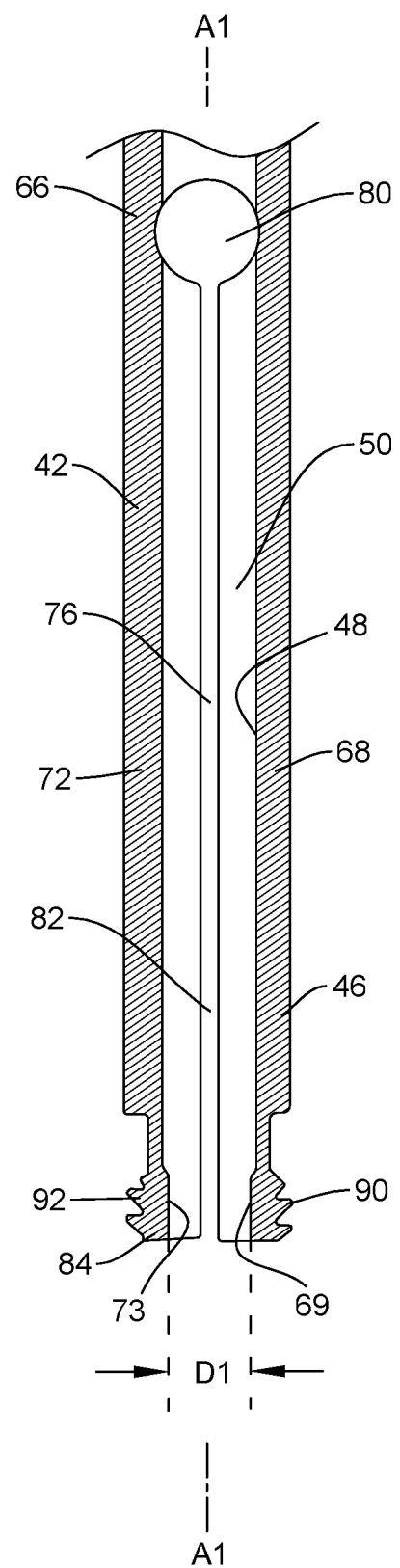
FIG. 11A is a side, cross-sectional view of the first component of the embodiment of the surgical system shown in FIG. 1, with the first component in a non-expanded configuration.

Gaps 76, 78 permit leg 68 move relative to leg 72 to move sleeve 42 between a non-expanded configuration and an expanded configuration to connect a component of system 40, such as, for example, an adapter 94 with sleeve 42, as discussed herein. That is, leg 68 is configured to move away from leg 72, or vice versa, to increase the width of portions 82, 88 and move sleeve 42 from the non-expanded configuration to the expanded configuration. In some embodiments, passageway 50 has a first diameter D1 between a distal inner surface 69 of leg 68 and a distal inner surface 73 of leg 72 when sleeve 42 is in the non-expanded configuration, as shown in FIG. 11A, and a second diameter D2 between distal inner surface 69 and distal inner surface 73 when sleeve 42 is in the expanded configuration, as shown in FIG. 11B, diameter D2 being greater than the diameter D1. When sleeve 42 is in the non-expanded configuration, distal inner surfaces 69, 73 each extend parallel to axis A1, as shown in FIG. 11A. When sleeve 42 is in the expanded configuration, distal inner surfaces 69, 73 each extend at an angle α relative to axis A1, as shown in FIG. 11B. In some embodiments, angle α is between about 1 degree and about 45 degrees. In some embodiments, angle α is between about 1 degree and about 10 degrees. In some embodiments, angle α is between about 1 degree and about 5 degrees.

In some embodiments, sleeve 42 will remain in the non-expanded configuration unless and until a force is applied to leg 68 and/or leg 72 to move sleeve 42 from the non-expanded configuration to the expanded configuration. In some embodiments, sleeve 42 is resiliently biased to the non-expanded configuration such that sleeve 42 will move from the expanded configuration to the non-expanded configuration after the force that moves sleeve 42 from the non-expanded configuration to the expanded configuration is removed. In some embodiments, end 46 includes a first threaded portion 90 on leg 68 and a second threaded portion 92 on leg 72. Threaded portions 90, 92 are spaced apart from one another by gaps 76, 78 and cooperate to define a mating element configured to engage a mating element of a component of system 40, such as, for example, a bone fastener 192 to connect bone fastener 192 with sleeve 42, as discussed herein.

Surgical system 40 includes a removable tip, such as, for example, adapter 94. Adapter 94 is configured to be removably coupled to sleeve 42. Adapter 94 extends along a longitudinal axis A2 between a proximal portion 96 and an opposite distal portion 98. Portion 96 includes a spherical component, such as, for example, a convexly curved circumferential shoulder 100 that extends outwardly from a body 102 of adapter 94. Shoulder 100 has a maximum diameter D3 that is greater than diameter D1 between distal inner surface 69 and distal inner surface 73 when sleeve 42 is in the non-expanded configuration, as shown in FIG. 11C. Diameter D3 is less than second diameter D2 between distal inner surface 69 and distal inner surface 73 when sleeve 42 is in the expanded configuration. In some embodiments, all or only a portion of shoulder 100 may be variously configured and dimensioned, such as, for example, planar, concave, polygonal, irregular, uniform, non-uniform, staggered, tapered, consistent or variable, depending on the requirements of a particular application. In some embodiments, axis A1 is coaxial with axis A2 when adapter 94 is coupled to sleeve 42.

To connect adapter 94 with sleeve 42, a force is applied to leg 68 and/or leg 72 to move leg 68 away from leg 72 such that sleeve 42 moves from the non-expanded configuration to the expanded configuration. In some embodiments, the force that is applied to leg 68 and/or leg 72 to move leg 68 away from leg 72 is provided by shoulder 100. That is, as shoulder 100 moves proximally relative to sleeve 42 to engage surfaces 69, 73, shoulder 100 moves leg 68 away from leg 72, or vice versa, to move sleeve 42 from the non-expanded configuration to the expanded configuration. As sleeve 42 moves from the non-expanded configuration to the expanded configuration, the diameter between distal inner surface 69 and distal inner surface 73 increases from diameter D1 to diameter D2. Since diameter D2 is greater than D3, shoulder 100 is able to be moved proximally passed distal inner surfaces 69,73 and into passageway 50. The force that was applied to leg 68 and/or leg 72 is removed to allow sleeve 42 to move from the expanded configuration to the non-expanded configuration. In some embodiments, removing the force that was applied to leg 68 and/or leg 72 comprises moving shoulder 100 passed distal inner surfaces 69,73 and into passageway 50. Because diameter D3 is less than diameter D1, sleeve 42 prevents adapter 94 from being removed from sleeve 42 when shoulder 100 is positioned within passageway 50. That is, sleeve 42 would have to be moved from the non-expanded configuration to the expanded configuration to remove adapter 94 from sleeve 42 when shoulder 100 is positioned within passageway 50. In some embodiments, surfaces 69, 73 directly engage an outer surface of body 102 and/or an outer surface of shoulder 100 directly engages inner surface 48 when shoulder 100 is positioned within passageway 50 and sleeve 42 is in the non-expanded configuration to provide a clamping force that fixes adapter 94 relative to sleeve 42. In one embodiment, distal ends of legs 68, 72 are configured for disposal in a channel 116 of adapter 94 such that legs 68, 72 snap into adapter 94. In one embodiment, distal ends of legs 68, 72 each include a male thread configured for engagement of a female thread defined by an inner surface 114 of adapter 94 to couple legs 68, 72 to adapter 94. In one embodiment, distal ends of legs 68, 72 each include a female thread configured for engagement of a male thread defined by an outer surface of adapter 94 to couple legs 68, 72 to adapter 94. In some embodiments, legs 68, 72 are coupled to adapter 94 by mutual grooves, screws, adhesive, nails, barbs, raised elements, spikes, clips, snaps, friction fittings, compressive fittings, expanding rivets, staples, fixation plates, key/keyslot, tongue in groove, dovetail, magnetic connection and/or posts.

Figure 12:
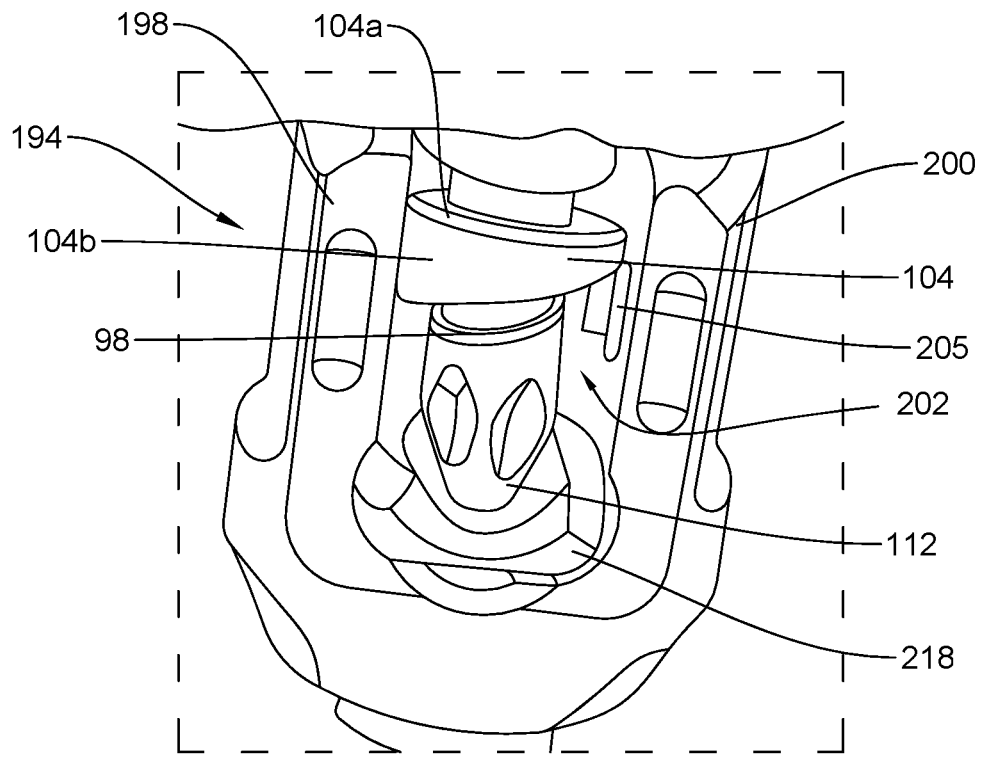
FIG. 12 is a first perspective view of components of the embodiment of the surgical system shown in FIG. 1.
Figure 13:
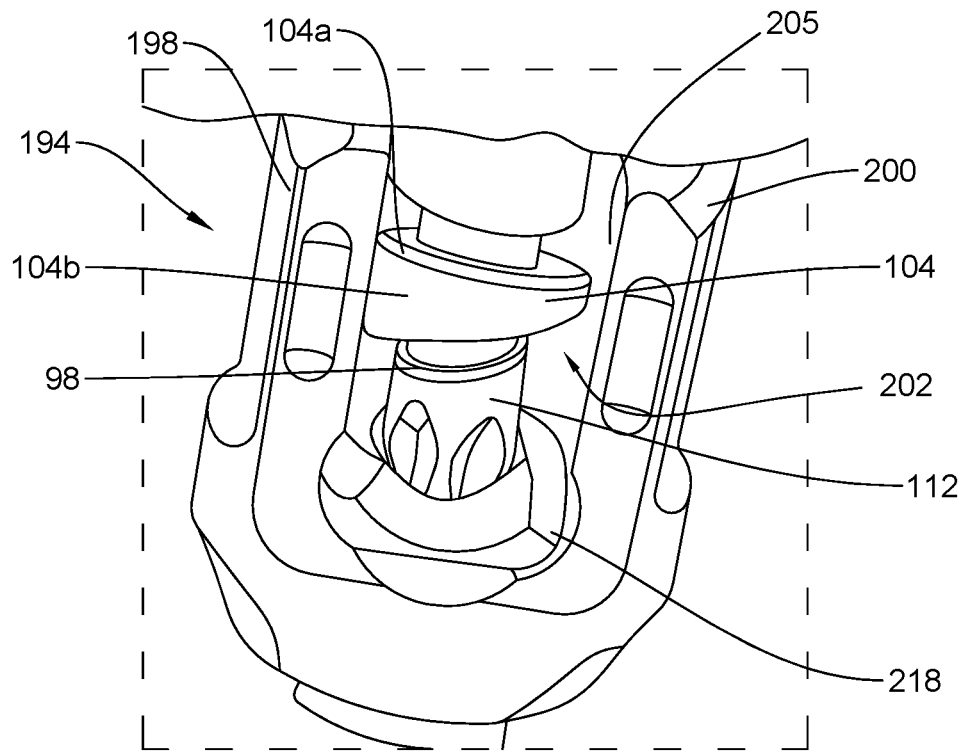
FIG. 13 is a second perspective view of components of the embodiment of the surgical system shown in FIG. 1.

Adapter 94 includes a first flange 104 extending from a first side 106 of body 102 and a second flange 108 extending from an opposite second side 110 of body 102. A top surface 104a of flange 104 and a top surface 108a of flange 108 each extend perpendicular to axis A2. In some embodiments, a side portion 104b of flange 104 and a side portion 108b of flange 108 each have a helical configuration, as shown in FIGS. 12 and 13 for example, to ensure the proper orientation of a tip 112 of adapter 94 when adapter 94 is assembled with a component of system 40, such as, for example, bone fastener 192, as discussed herein. For example, the helical configuration of flanges 104, 108 provides a helical sweep that helps reorient adapter 94 as adapter 94 is coupled to bone fastener 192 by converting a downward force into a twist, as discussed herein. Tip 112 defines a drive portion configured for engagement with a component of system 40, such as, for example, a screw shaft 196 of bone fastener 192 to drive screw shaft 196 into tissue, for example, as discussed herein. In some embodiments, surface 104a and/or surface 108a may be disposed at alternate orientations, relative to axis A2, such as, for example, transverse, perpendicular and/or other angular orientations such as acute or obtuse, co-axial and/or may be offset or staggered. In some embodiments, portion 104b and/or portion 108b may be variously configured and dimensioned, such as, for example, planar, concave, polygonal, irregular, uniform, non-uniform, staggered, tapered, consistent or variable, depending on the requirements of a particular application. In some embodiments, the drive portion may include a square, triangular, polygonal, star or hexalobe cross sectional configuration configured engage a correspondingly shaped portion of the component.

Figure 4:
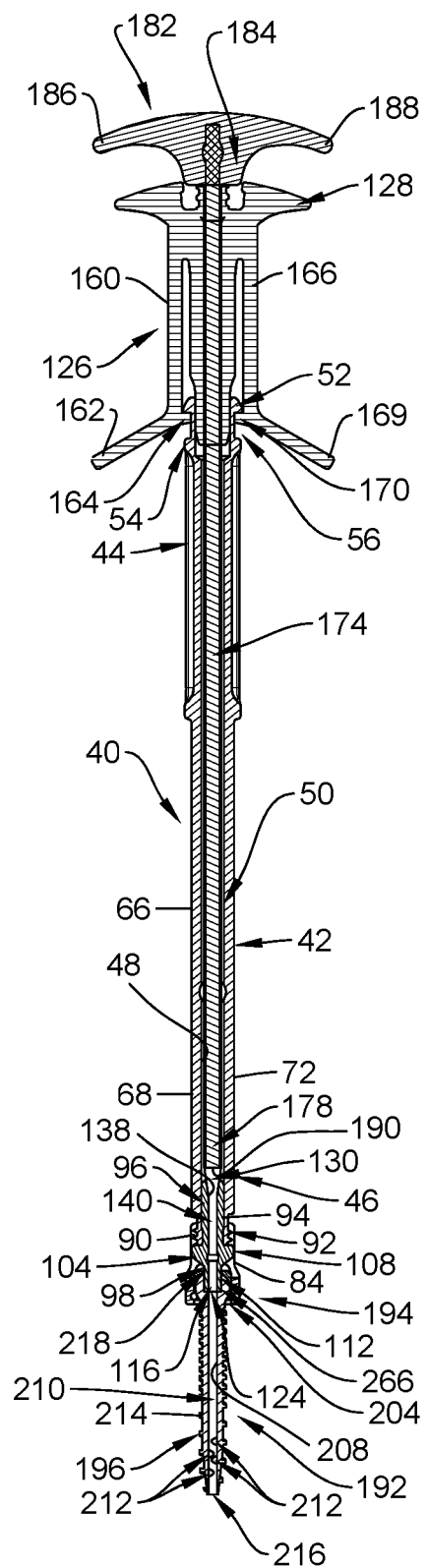
FIG. 4 is a second, cross-sectional view of components of the embodiment of the surgical system shown in FIG. 2.
Figure 4A:
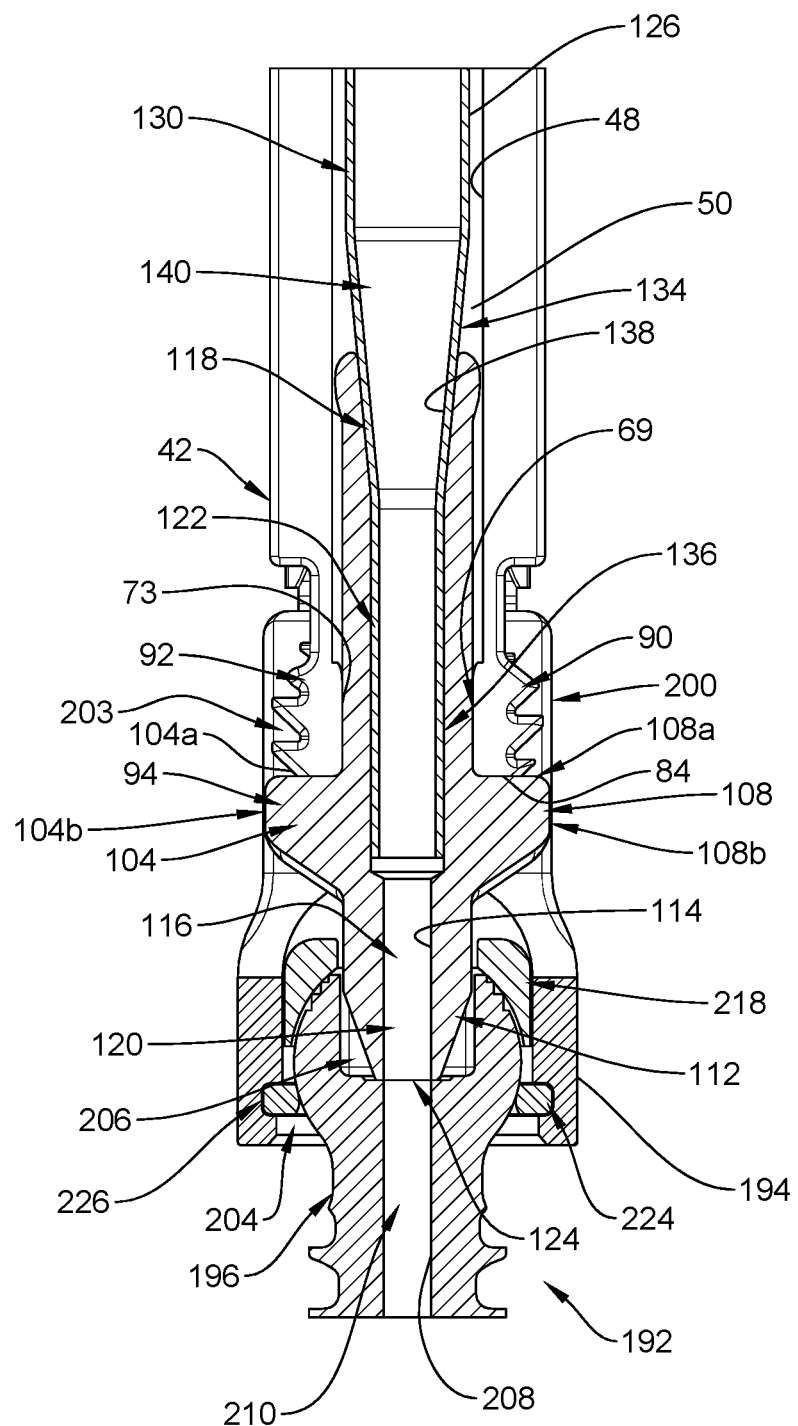
FIG. 4A is an enlarged, breakaway, cross-sectional view of components of the embodiment of the surgical system shown in FIG. 4.

Adapter 94 includes an inner surface 114 defining a channel 116 that extends through the entire length of adapter 94. Channel 116 extends parallel to axis A2. In some embodiments, channel 116 is coaxial with axes A1, A2 when adapter 94 is coupled to sleeve 42. Channel 116 is in communication with passageway 50 when shoulder 110 is positioned in passageway 50, as shown in FIG. 11C, for example. In some embodiments, channel 116 includes a tapered section 118, a first cylindrical section 120 and a second cylindrical section 122 that extends from tapered section 118 to cylindrical section 120, as shown in FIGS. 4A and 11C, for example. Section 122 has a maximum diameter that is greater than a maximum diameter of section 120 and section 118 has a maximum diameter that is greater than the maximum diameter of section 122. Section 118 and section 122 are configured to match the configuration of a tip of a component of system 40, such as, for example, delivery device 126 when the tip of delivery device 126 is positioned within section 118 and section 122 to inject a material into portion 120 of channel 116. Due to the decreased diameter of section 120 relative to section 122, the material will be under a greater amount of pressure as the material moves distally from section 122 and into section 120. In some embodiments, the increased pressure will assist in moving the material out of channel 116 through a distal orifice 124 of tip 112. In some embodiments, section 118, section 120 and/or section 122 may have various cross section configurations, such as, for example, oval, oblong, triangular, rectangular, square, polygonal, irregular, uniform, non-uniform, variable, tubular and/or tapered.

Delivery device 126 extends along a longitudinal axis A3 between a handle 128 and a shaft 130. Shaft 130 is configured to be movably positioned in passageway 50 such that a distal end 132 of shaft 130 is positioned within channel 116. In some embodiments, axis A3 is coaxial with axis A1 when shaft 130 is positioned in passageway 50. End 132 includes a tapered portion 134 configured for disposal in tapered section 118 of channel 116 and a cylindrical portion 136 configured for disposal in cylindrical section 122 of channel 116. In some embodiments, an outer surface of portion 134 directly engages the inner surface of adapter 94 that defines section 118 such that the outer surface of portion 134 and the inner surface of adapter 94 form a fluid-tight seal and/or an outer surface of portion 136 directly engages the inner surface of adapter 94 that defines section 122 such that the outer surface of portion 136 and the inner surface of adapter 94 form a fluid-tight seal to prevent a material that is moved through shaft 130 and into channel 116 from leaking within and/or into passageway 50. Shaft 130 includes an inner surface 138 defining a lumen 140 that extends the entire length of shaft 130. Lumen 140 is coaxial with axis A3. In some embodiments, tapered portion 134 has a maximum diameter that is greater than a maximum diameter of cylindrical portion 136 such that a material that moves distally through lumen 140 will increase in pressure as the material moves from tapered portion 134 to cylindrical portion 136. In some embodiments, lumen 140 may be disposed at alternate orientations, relative to axis A3, such as, for example, transverse, perpendicular and/or other angular orientations such as acute or obtuse, co-axial and/or may be offset or staggered.

Handle 128 comprises a body 142 including a cylindrical portion 144 that is coaxial with shaft 130 and axis A3. Cylindrical portion 144 has a threaded outer surface 146 and an opposite inner surface defining an opening 148 that is in communication and coaxial with lumen 140 and axis A3. Body 142 comprises a conical portion 150 opposite cylindrical portion 144. Conical portion 150 is configured for disposal in passageway 50 to connect handle 128 with sleeve 42, as discussed herein. Conical portion 150 helps facilitate axialization of device 126 relative to sleeve 42 to ensure proper assembly. In some embodiments, threaded outer surface 146 is configured for engagement with a component of system 40, such as, for engagement with a threaded surface of a cement delivery system to connect the cement delivery system with delivery device 126. In some embodiments, delivery device 126 can be variously connected with the cement delivery system, such as, for example, monolithic, integral connection, frictional engagement, threaded engagement, mutual grooves, screws, adhesive, nails, barbs and/or raised element.

Handle 128 comprises a mating element that is configured to engage the mating element of sleeve 42 that includes flange 52. The mating element of handle 128 includes a first wing 152 that extends from a first side 154 of body 142 in a cantilevered configuration and a second wing 156 that extends from an opposite second side 158 of body 142 in a cantilevered configuration. Wing 152 comprises an extension 160 that extends from first side 154, a gripping portion 162 that extends from extension 160 and a tab 164 that extends from extension 160. Wing 156 comprises an extension 166 that extends from second side 158, a gripping portion 168 that extends from extension 166 and a tab 170 that extends from extension 166. Extensions 160, 166 each extend parallel to axis A3. Gripping portions 162, 168 each extend transverse to axis A3. Tabs 164, 170 each extend perpendicular to axis A3. Tab 164 includes a surface 164*a* that extends parallel to axis A3 and tab 170 includes a surface 170*a* that extends parallel to axis A3. Surface 164*a* faces surface 170*a*. Tab 164 includes a surface 164*b* that extends perpendicular to axis A3 and tab 170 includes a surface 147*b* that extends perpendicular to axis A3. Tabs 164, 170 are configured to engage flange 52 to secure the device 126 to sleeve 42 such that device 126 is prevented from translating axially relative to sleeve 42 in the direction shown by arrow A in FIG. 20. Surface 164*a* is spaced a first distance apart from surface 170*a* when no forces are applied to wings 152, 156. Wings 152, 156 are configured to deflect relative to body 142. For example, a force may be applied to gripping portion 162 to move gripping portion 162 relative to body 142 in the direction shown by arrow B in FIG. 18 and a force may be applied to gripping portion 168 to move gripping portion 168 relative to body 142 in the direction shown by arrow C in FIG. 18 such that tabs 164, 170 move away from one another and surface 164*a* is spaced an increased second distance apart from surface 170*a*. In some embodiments, wings 152, 156 are resiliently biased inwardly such that after the forces are removed from gripping portions 162, 168, tab 164 moves toward tab 170, or vice versa, such that surface 164*a* is spaced the first distance apart from surface 170*a*.

To connect device 126 with sleeve 42, shaft 130 is inserted into passageway 50 such that axis A3 is coaxial with axis A1. Device 126 is then translated axially relative to sleeve 42 in the direction shown by arrow D in FIG. 19 until conical portion 150 is positioned within passageway 50. As device 126 translates axially relative to sleeve 42 in the direction shown by arrow D in FIG. 19, surface 164*b* of tab 164 slides along surface 62 of flange 52 and surface 170*b* of tab 170 slides along surface 62. As surfaces 164*b*, 170*b* slide along surface 62, wings 152, 156 deflect outwardly from body 142 such that the distance between surfaces 164*b*, 170*b* increases from the first distance to a second distance. Device 126 is further translated axially relative to sleeve 42 in the direction shown by arrow D in FIG. 19 when surfaces 164*b*, 170*b* are spaced apart by the second distance such that surfaces 164*b*, 170*b* slide along surface 64 of flange 52. Device 126 is further translated axially relative to sleeve 42 in the direction shown by arrow D in FIG. 19 such that tabs 164, 170 are aligned with recess 56. The inward bias of wings 152, 156 causes tabs 164, 170 to move toward one another such that surface 164*b* is spaced the first distance apart from surface 170*b* and surfaces 164*a*, 170*a* engage surface 60 of flange 52 to prevent device 126 from translating axially relative to sleeve 42 in the direction shown by arrow A in FIG. 20. In some embodiments, tabs 164, 170 create a clicking sound when tabs 164, 170 move toward one another and surfaces 164*a*, 170*a* engage surface 60 of flange 52, which indicates the device 126 is properly assembled with sleeve 42.

Figure 18:
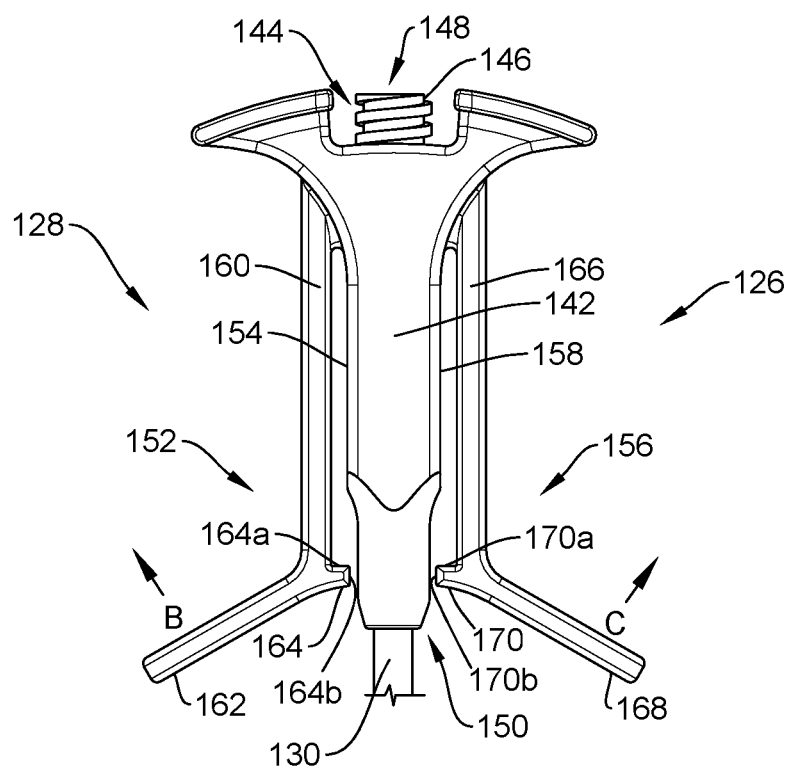
FIG. 18 is a side, breakaway view of the third component of the embodiment of the surgical system shown in FIG. 1.
Figure 19:
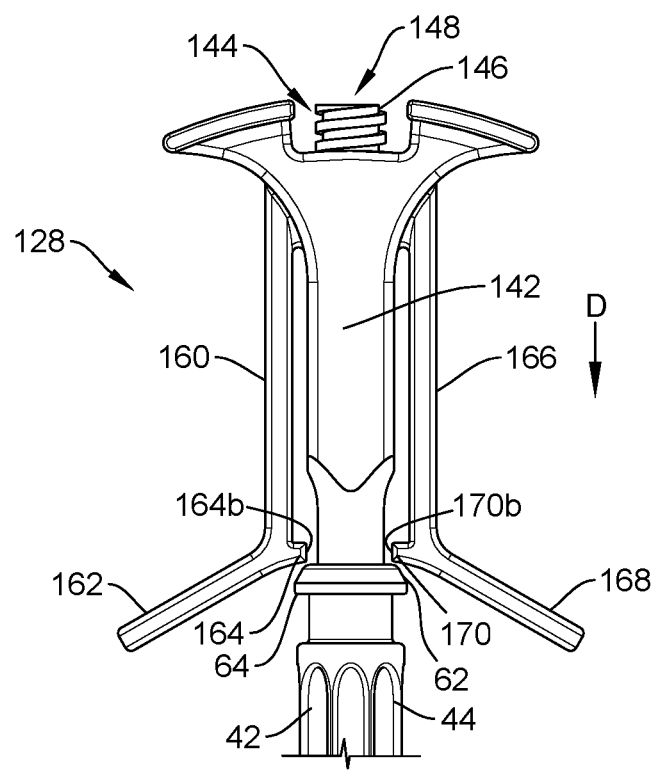
FIG. 19 is a side view of the first and third components of the embodiment of the surgical system shown in FIG. 1, with the first and third components in a first position.
Figure 20:
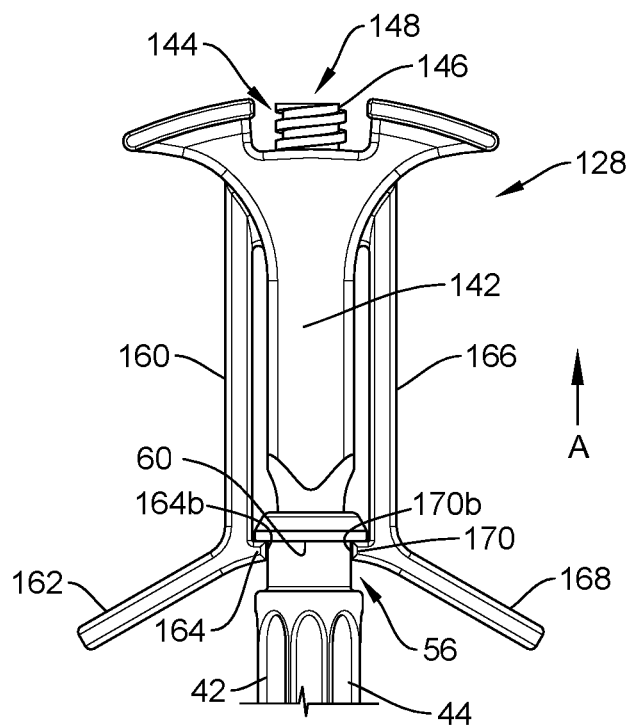
FIG. 20 is a side view of the first and third components of the embodiment of the surgical system shown in FIG. 1, with the first and third components in a second position.

To remove device 126 from sleeve 42, a force is applied to gripping portion 162 to move gripping portion 162 relative to body 142 in the direction shown by arrow B in FIG. 18 and a force is applied to gripping portion 168 to move gripping portion 168 relative to body 142 in the direction shown by arrow C in FIG. 18 such that surface 164*b* is spaced the second distance apart from surface 170*b*. Device 126 is translated axially relative to sleeve 42 in the direction shown by arrow A in FIG. 20 such that surfaces 164*b*, 170*b* slide along surface 64. Device 126 may be translated axially relative to sleeve 42 in the direction shown by arrow A in FIG. 20 until shaft 130 is completely removed from passageway 50.

Surgical system 40 includes a plunger 172 having a shank 174 extending along a longitudinal axis A4 between a proximal end 176 and an opposite distal end 178. Shank 174 is configured for movable disposal in lumen 140 to move a material, such as, for example, bone cement through lumen 140 such that the material exits lumen 140 and moves into channel 116, as discussed herein. In some embodiments, shank 174 has a cylindrical configuration and a uniform diameter along the entire length of shank 174. In some embodiments, shank 174 is completely solid and/or is free of any gaps or openings through any part of shank 174 and/or along the entire length of shank 174. In some embodiments, shank 174 includes one or a plurality of graduation markings 180 along shank 174 configured to measure the depth that shank 174 is inserted into lumen 140. That is, graduation markings 180 can provide a surgeon visual confirmation regarding the length of shank 174 that has been inserted into lumen 140. In embodiments wherein the shank comprises a plurality of graduation markings 180, graduation markings 180 are spaced apart from one another along the length of shank 174. In some embodiments, graduation markings 180 can be used to determine the amount of bone cement that has pushed out of lumen 140 and into channel 116. For example, aligning a first graduation marking 180a with a top surface 144a of portion 144 can indicate that a first amount of bone cement has pushed out of lumen 140 and into channel 116 and aligning a second graduation marking 180b with surface 144a can indicate that a second amount of bone cement has pushed out of lumen 140 and into channel 116, the second amount being greater than the first amount. End 178 includes an end surface 190 that extends perpendicular to axis A4. In some embodiments, end surface 190 has a solid configuration that is free of any gaps or openings such that end surface 190 is configured to push the material through lumen 140. In some embodiments, end surface 190 may be disposed at alternate orientations, relative to axis A4, such as, for example, transverse, perpendicular and/or other angular orientations such as acute or obtuse, co-axial and/or may be offset or staggered. In some embodiments, shank 174 includes a male thread along shank 174 configured to engage a female thread of defined by surface 138 such that shank 174 can be incrementally advanced within lumen 140 by rotating shank 174 relative to shaft 130. It is envisioned that the engagement of the male thread of shank 174 with the female thread of surface 138 will prevent unintended translation of shank 174 relative to shaft 130 in a first axial direction and an opposite second axial direction. In some embodiments, shank 174 is rotated relative to shaft 130 until first graduation marking 180a is aligned with surface 144a of portion 144 to indicate that the first amount of bone cement has been pushed out of lumen 140.

Plunger 172 includes a handle 182 that is coupled to shank 174. In some embodiments, handle 182 is fixed to shank 174 and is configured for gripping by a medical practitioner to all the medical practitioner to guide shank 174 through opening 148 and into lumen 140 and to move shank 174 axially within lumen 140, as discussed herein. Handle 182 includes a body 184 that is directly coupled to shank 174, a first arm 186 extending from a first side of body 184 and a second arm 188 extending from an opposite second side of body 184. Arms 186, 188 are configured for gripping by the fingers of a medical practitioner to move shank 174 axially in opposite directions within lumen 140, as discussed herein. In some embodiments, handle 182 is integrally and/or monolithically formed with shank 174. In some embodiments, handle 182 is removable shank 174 to allow shank 174 to be coupled with different handles, such as, for example, different handles of different sizes and/or shapes. In some embodiments, handle 182 includes a threaded inner surface that is configured to mate with threaded outer surface 146 to couple plunger 172 to handle 128 in a manner that prevents plunger 172 from moving axially relative to delivery device 126. In some embodiments, plunger 172 can be variously connected with delivery device 126 to prevent plunger 172 from moving axially relative to delivery device 126, such as, for example, frictional engagement, mutual grooves, screws, adhesive, nails, barbs and/or raised element.

Bone fastener 192 includes a head, such as, for example, an implant receiver 194 and a shank, such as, for example, a screw shaft 196 that is coupled to receiver 194 and defines a longitudinal axis A5. Implant receiver 194 includes a pair of spaced apart arms 198, 200 that define an implant cavity 202 therebetween configured for disposal of a spinal construct, such as, for example, a spinal rod. Arms 198, 200 each extend parallel to one another. In some embodiments, arm 198 and/or arm 200 may be disposed at alternate orientations, such as, for example, transverse, perpendicular and/or other angular orientations such as acute or obtuse, coaxial and/or may be offset or staggered. Arms 198, 200 each include an arcuate outer surface extending between a pair of side surfaces. At least one of the outer surfaces and the side surfaces of arms 198, 200 have at least one recess or cavity therein configured to receive an insertion tool, compression instrument and/or instruments for inserting and tensioning bone fastener 192.

Cavity 202 is substantially U-shaped. In some embodiments, all or only a portion of cavity 202 may have alternate cross section configurations, such as, for example, closed, V-shaped, W-shaped, oval, oblong triangular, square, polygonal, irregular, uniform, non-uniform, offset, staggered, and/or tapered. Implant receiver 194 includes thread forms 203, 205 configured for engagement with a coupling member, such as, for example, a setscrew to retain a spinal rod within cavity 202. Thread forms 203, 205 also define a mating element configured to engage the mating element of sleeve 42 that includes threaded portions 90, 92 to couple sleeve 42 to implant receiver 194, as discussed herein. In some embodiments, the inner surface of implant receiver 194 may be disposed with the coupling member and/or sleeve 42 in alternate fixation configurations, such as, for example, friction fit, pressure fit, locking protrusion/recess, locking keyway and/or adhesive. In some embodiments, all or only a portion of the inner surface of implant receiver 194 may have alternate surface configurations to enhance engagement with a spinal rod, a setscrew and/or sleeve 42, such as, for example, rough, arcuate, undulating, mesh, porous, semi-porous, dimpled and/or textured. In some embodiments, implant receiver 194 may include alternate configurations, such as, for example, closed, open and/or side access.

Figure 15:
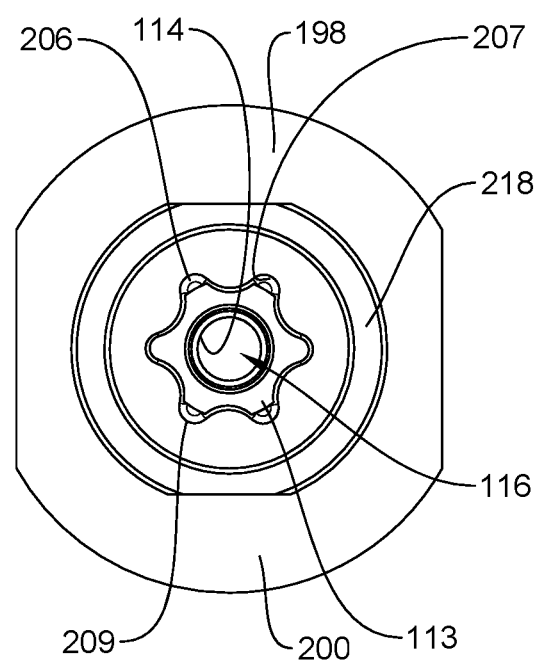
FIG. 15 is a second top view of the second and fifth components of the embodiment of the surgical system shown in FIG. 1.

Implant receiver 194 defines a cavity 204 configured for disposal of a head of screw shaft 196, as described herein. Screw shaft 196 includes a tool engaging portion, such as, for example, a socket 206 configured to disposal of the drive portion of tip 112. Socket 206 is coaxial with axis A5. In some embodiments, tip 112 is configured for disposal in socket 206 such that tip 112 is rotatable within socket 206. In some embodiments, tip 112 is configured for disposal in socket 206 such that tip 112 engages a surface 207 of screw shaft 196 that defines socket 206 and rotation of adapter 94 also rotates screw shaft 196. That is, adapter 94 is not rotatable relative to screw shaft 196 while tip 112 is positioned within socket 206. In some embodiments, tip 112 includes a plurality of spaced apart lobes 113 that are each configured for disposal in one of a plurality of spaced apart lobes 209 of socket 206, as shown in FIG. 15, to prevent rotation of tip 112 relative to screw shaft 196 when tip 112 is disposed in socket 206 such that rotation of adapter 94 also rotates screw shaft 196.

Screw shaft 196 includes an outer surface having an external thread form. In some embodiments, the external thread form may include a single thread turn or a plurality of discrete threads. Screw shaft 196 includes an inner surface 208 defining a cannula 210 (FIG. 4A) that extends the entire length of screw shaft 196. Cannula 210 is coaxial with axis A5. When the drive portion of tip 112 engages tool engaging portion 206, channel 116 is in communication and coaxial with cannula 210. In some embodiments, screw shaft 196 includes one or a plurality of openings or fenestrations 212 that each extend through surface 208 and an opposite outer surface 214 of screw shaft 196 such that a material, such as, for example, bone cement disposed in cannula 210 can exit cannula 210 through one of fenestrations 212 and/or through an opening 216 in a distal end of screw shaft 196. In some embodiments, at least one of fenestrations 212 is positioned between crests of the external thread form. In some embodiments, at least one of fenestrations 212 extends through a crest of the external thread form. In some embodiments, fenestrations 212 are disposed radially about screw shaft 196. In some embodiments, screw shaft 196 includes only a plurality of spaced apart column of fenestrations 212, the columns each being disposed axially along screw shaft 196. In some embodiments, screw shaft 196 includes only a single column of fenestrations 212 that are disposed axially along screw shaft 196 such that fenestrations 212 each face the same direction to direct bone cement in the direction that fenestrations 212 face. In some embodiments, at least one of fenestrations 212 extends perpendicular to axis A5. In some embodiments, at least one of fenestrations 212 extends transverse to axis A5, such as, for example, at an acute angle relative to axis A5.

Figure 9:
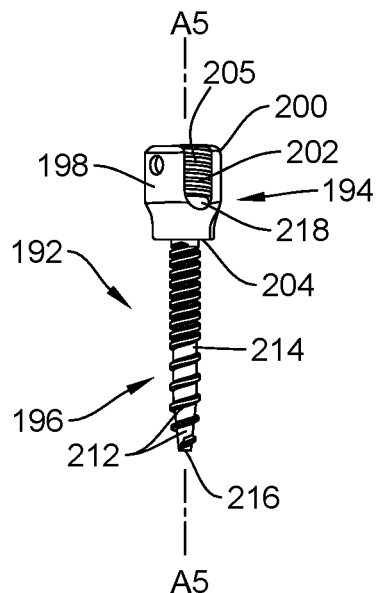
FIG. 9 is a side view of one embodiment a fifth component of the embodiment of the surgical system shown in FIG. 1, in accordance with the principles of the present disclosure.
Figure 9A:
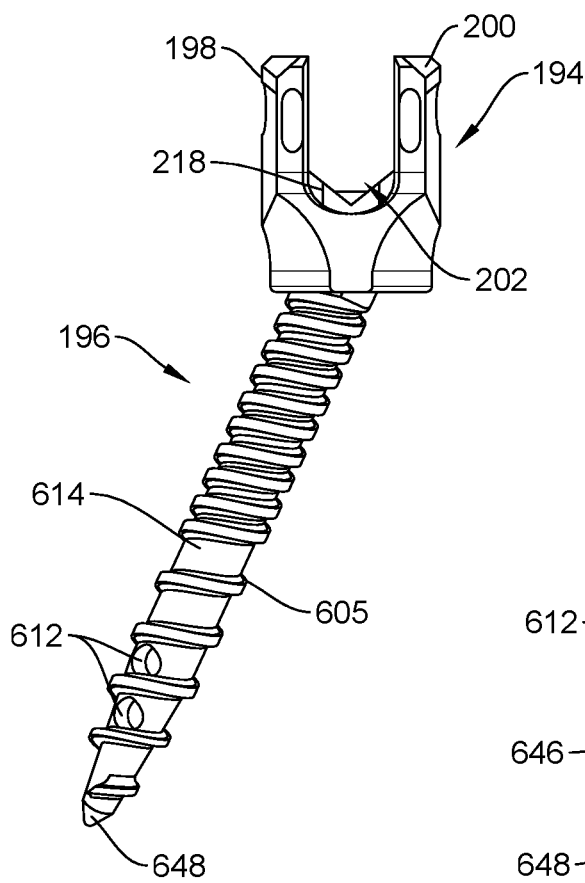
FIG. 9A is a side view of one embodiment the fifth component of the embodiment of the surgical system shown in FIG. 1, in accordance with the principles of the present disclosure.
Figure 9B:
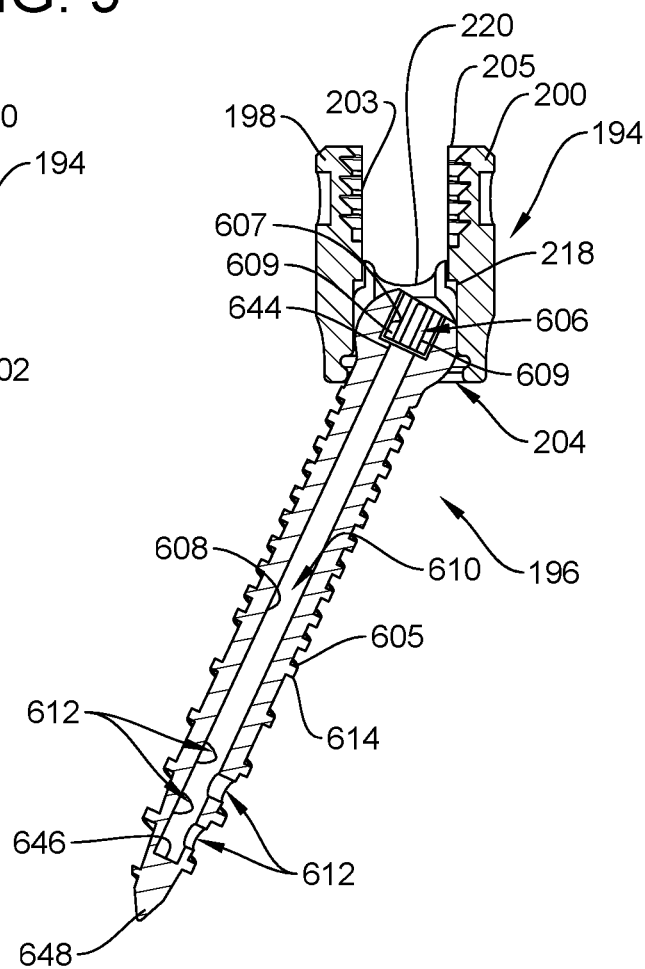
FIG. 9B is a side, cross-sectional view of the fifth component shown in FIG. 9A.

In one embodiment, shown in FIGS. 9A and 9B, screw shaft 196 includes a tool engaging portion, such as, for example, a socket 606 configured to engage the drive portion of tip 112. In some embodiments, tip 112 is configured for disposal in socket 606 such that tip 112 is rotatable within socket 606. In some embodiments, tip 112 is configured for disposal in socket 606 such that tip 112 engages a surface 607 of screw shaft 196 that defines socket 606 and rotation of adapter 94 also rotates screw shaft 196. In some embodiments, lobes 113 are each configured for disposal in one of a plurality of spaced apart lobes 609 of socket 606 to prevent rotation of tip 112 relative to screw shaft 196 when tip 112 is disposed in socket 606 such that rotation of adapter 94 also rotates screw shaft 196.

Screw shaft 196 includes an outer surface having an external thread form 605. In some embodiments, the external thread form may include a single thread turn or a plurality of discrete threads. Screw shaft 196 includes an inner surface 608 defining a cannula 610 (FIG. 9B) that extends less than the entire length of screw shaft 196, as discussed herein. When the drive portion of tip 112 engages tool engaging portion 606, channel 116 is in communication and coaxial with cannula 610. In some embodiments, screw shaft 196 includes one or a plurality of openings or fenestrations 612 that each extend through surface 608 and an opposite outer surface 614 of screw shaft 196. Fenestrations 612 are in communication with cannula 610. Surface 608 extends between a proximal end 644 and a distal most end 646. Cannula 610 includes a closed configuration adjacent a proximal end of a tip 648, as described herein. End 646 is disposed in a spaced apart relation relative to a distal end of tip 648. This configuration of end 646 and tip 648 resist and/or prevent the release of an agent external and/or outside of a vertebral body. As such, the agent can be confined within the vertebral body to resist and/or prevent leakage to non-select body regions. A material, such as, for example, bone cement disposed in cannula 610 can exit cannula 610 through one of fenestrations 612. Due to the closed configuration of cannula 610 adjacent a proximal end of a tip 648, the bone cement is prevented from exiting cannula 610 through tip 648. In some embodiments, at least one of fenestrations 612 is positioned between crests of external thread form 614. In some embodiments, at least one of fenestrations 612 extends through a crest of external thread form 614. In some embodiments, fenestrations 612 are disposed radially about screw shaft 196. In some embodiments, screw shaft 196 includes only a plurality of spaced apart column of fenestrations 612, the columns each being disposed axially along screw shaft 196. In some embodiments, screw shaft 196 includes only a single column of fenestrations 612 that are disposed axially along screw shaft 196 such that fenestrations 612 each face the same direction to direct bone cement in the direction that fenestrations 612 face. In some embodiments, at least one of fenestrations 612 extends perpendicular to axis A5. In some embodiments, at least one of fenestrations 612 extends transverse to axis A5, such as, for example, at an acute angle relative to axis A5.

In some embodiments, implant receiver 194 is manually engageable with screw shaft 196 in a non-instrumented assembly, as described herein. In some embodiments, manual engagement and/or non-instrumented assembly of implant receiver 194 and screw shaft 196 includes coupling without use of separate and/or independent instrumentation engaged with the components to effect assembly. In some embodiments, manual engagement and/or non-instrumented assembly includes a practitioner, surgeon and/or medical staff grasping implant receiver 194 and screw shaft 196 and forcibly assembling the components. In some embodiments, manual engagement and/or non-instrumented assembly includes a practitioner, surgeon and/or medical staff grasping implant receiver 194 and screw shaft 196 and forcibly snap fitting the components together, as described herein. In some embodiments, manual engagement and/or non-instrumented assembly includes a practitioner, surgeon and/or medical staff grasping implant receiver 194 and screw shaft 196 and forcibly pop fitting the components together and/or pop fitting implant receiver 194 onto screw shaft 196, as described herein. In some embodiments, a force in a range of 2-50 N is required to manually engage implant receiver 194 and screw shaft 196 and forcibly assemble the components. In some embodiments, a force in a range of 5-10 N is required to manually engage implant receiver 194 and screw shaft 196 and forcibly assemble the components.

In some embodiments, implant receiver 194 is connectable with screw shaft 196 such that screw shaft 196 is pivotable and/or rotatable relative to implant receiver 194 in a plurality of planes. In some embodiments, implant receiver 194 is connectable with screw shaft 196 to include various configurations, such as, for example, a posted screw, a pedicle screw, a bolt, a bone screw for a lateral plate, an interbody screw, a uni-axial screw (UAS), a fixed angle screw (FAS), a multi-axial screw (MAS), a side loading screw, a sagittal adjusting screw (SAS), a transverse sagittal adjusting screw (TSAS), an awl tip screw (ATS), a dual rod multi-axial screw (DRMAS), midline lumbar fusion screw and/or a sacral bone screw.

Figure 14:
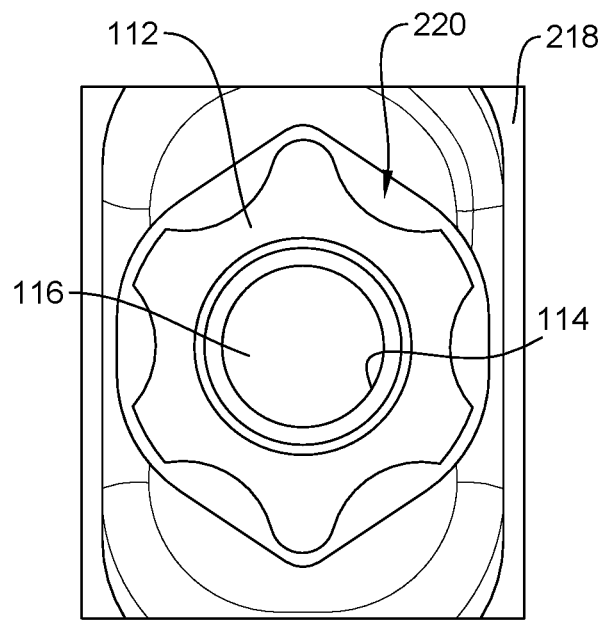
FIG. 14 is a first top view of the second and fifth components of the embodiment of the surgical system shown in FIG. 1.
Figure 16:
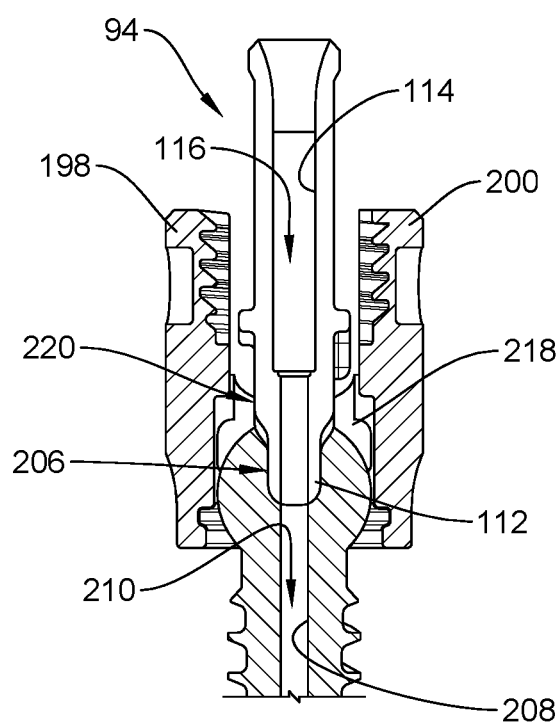
FIG. 16 is a side, cross-sectional view of the second and fifth components of the embodiment of the surgical system shown in FIG. 1.

Bone fastener 192 includes a saddle 218 configured for disposal in cavity 202 such that a bottom surface of saddle 218 directly engages the head of screw shaft 196. In some embodiments, saddle 218 is movable relative to receiver 194 to provide vertebral body control with accommodation of rod seating and allow a medical practitioner the ability to position bone fastener 192 in the natural kyphotic (outward) and lordoditc (inward) curve of the spine. Saddle 218 includes an aperture 220 that extends through a thickness of saddle 218. Aperture 220 is configured for disposal of tip 112 to allow tip 112 to extend through aperture 220 and into socket 606 or socket 206, as shown in FIGS. 14-16, for example. In some embodiments, tip 112 forms a seal with bone fastener 192 as tip 112 passes through saddle 218 and enters socket 206 or socket 606. In some embodiments, aperture 220 may have various cross section configurations, such as, for example, circular, oval, oblong, triangular, rectangular, square, polygonal, irregular, uniform, non-uniform, variable, tubular and/or tapered.

Bone fastener 192 includes a band, such as, for example, a ring 224 configured for disposal in a groove 226 of receiver 194 to retain screw shaft 196 with receiver 194. In some embodiments, ring 224 is C-shaped and includes a gap between opposite ends of ring 224. Ring 224 is configured to engage an outer surface of the head of screw shaft 196 and is disposable with groove 226 to prevent axial translation of screw shaft 196 relative to receiver 194 and facilitate rotation of screw shaft 196 relative to receiver 194. In some embodiments, ring 224 is disposed within receiver 194 to enhance a retaining strength of bone fastener 192 and resist and/or prevent shearing of screw shaft 196. In some embodiments, bone fastener 192 is assembled by coupling saddle 218 to the head of screw shaft 196 such that aperture 220 is aligned with socket 206 and inserting the head of screw shaft 196 proximally into cavity 204. Ring 224 is then positioned about screw shaft 196 and screw shaft 196 is moved proximally through cavity 204 and into groove 224 such that ring 224 is seated within groove 226 to prevent the head of screw shaft 196 from moving distally relative to receiver 194.

In assembly, operation and use, access to the surgical site is obtained and the particular surgical procedure is performed. The components of surgical system 40 are employed to augment the surgical treatment. For example, adapter 94 is coupled to sleeve 42, as discussed herein, such that end surface 84 directly engages top surface 104a of flange 104 and top surface 108a of flange 108 and channel 116 is in communication with passageway 50, as shown in FIG. 4A.

Bone fastener 192 is assembled in the manner discussed herein. Screw shaft 196 is selectively positioned adjacent tissue, such as, for example, bone. In some embodiments, a distal tip of screw shaft 196 is inserted into a pilot hole that was formed in the bone. Screw shaft 196 is rotated relative to the bone to drive screw shaft 196 into bone by inserting a bit of an insertion instrument, such as, for example, a screwdriver into socket 206 and rotating the screwdriver such that the screwdriver rotates screw shaft 196. As screw shaft 196 is rotate by the screwdriver, screw shaft 196 translates relative to the bone.

Once screw shaft 196 is driven a selected amount into bone, bone fastener 192 is then connected with sleeve 42 and adapter 94 by positioning flanges 104, 108 between arms 198, 200 to prevent rotation of adapter 94 relative to sleeve 42. Sleeve 42 and adapter 94 are translated distally relative to receiver 194 until threaded portions 90, 92 are positioned adjacent to thread forms 203, 205. The helical configurations of portions 104b, 108b of flanges 104, 108 maintain the orientation of tip 112 such that channel 116 remains coaxial with passageway 50 as sleeve 42 and adapter 42 are connected with bone fastener 192, as discussed herein. Sleeve 42 is rotated relative to receiver 194 such that threaded portions 90, 92 mate with thread forms 203, 205 to fix sleeve 42 and adapter 94 relative to receiver 194. Sleeve 42 is rotated relative to receiver 194 until tip 112 extends through aperture 220 and tip 112 is disposed in socket 206 such that the drive portion of tip 112 engages the tool engagement portion of socket 206 to prevent rotation of tip 112 relative to screw shaft 196, tip 112 forms a seal with socket 206, and channel 116 is in communication with cannula 210. In some embodiments, the seal formed by tip 112 and socket 206 ensures that any material that moves through orifice 124 will move directly into cannula 210 and will not exude into socket 206.

Delivery device 126 is coupled with sleeve 42 by inserting shaft 130 into passageway 50 and moving shaft 130 distally within passageway 50 until portion 136 is disposed in channel 116 such that lumen 140 is in communication with channel 116 and shaft 130 creates a fluid-tight seal with adapter 94, as discussed herein.

Figure 21A:
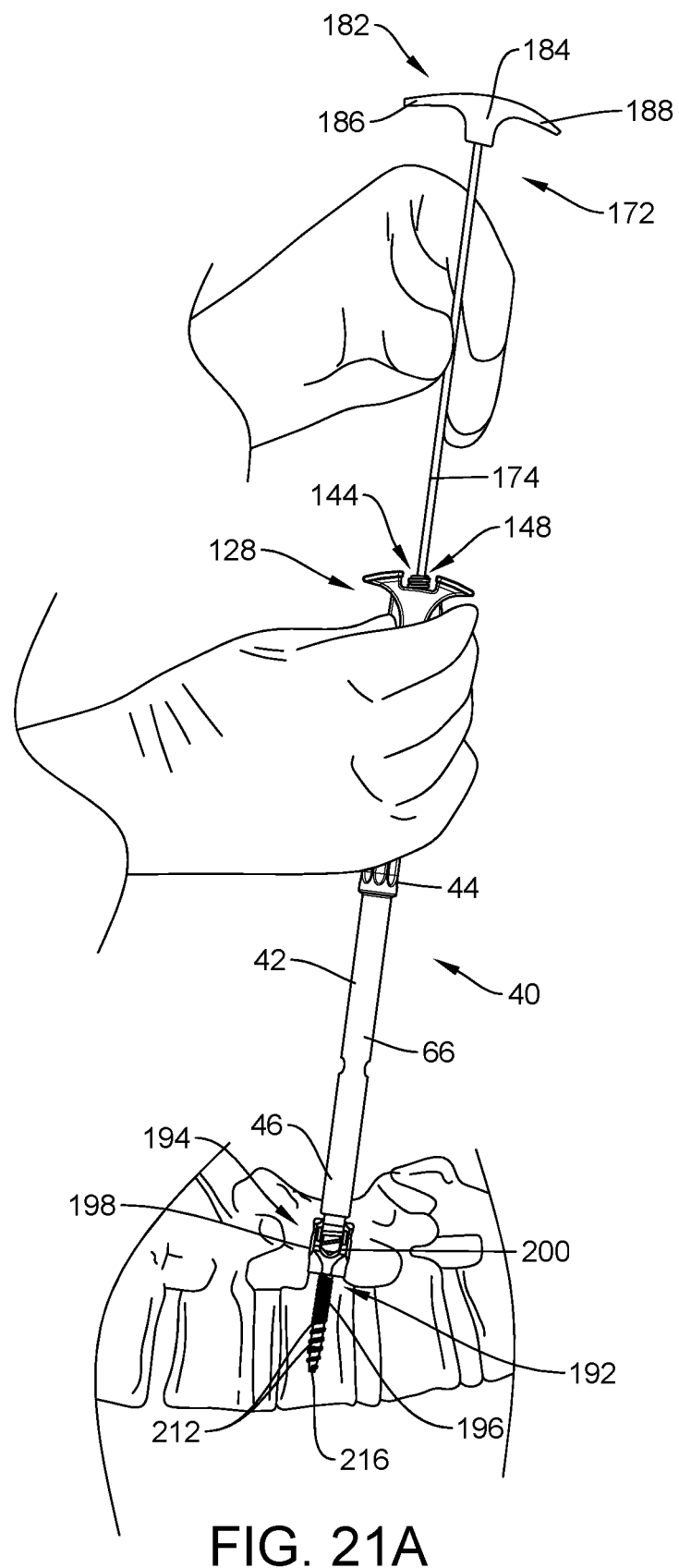
FIG. 21A is a plan view of the embodiment of the surgical system shown in FIG. 1, with the fourth component inserted into the first component a first amount.
Figure 21B:
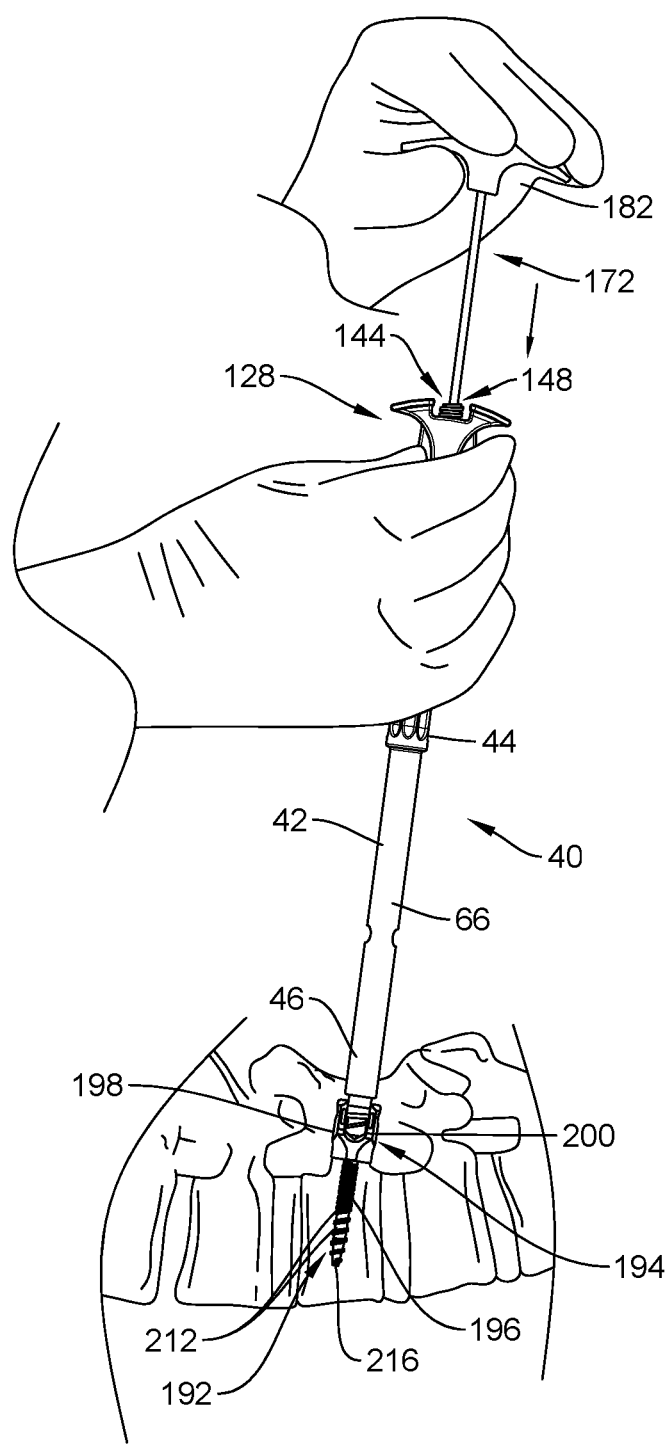
FIG. 21B is a plan view of the embodiment of the surgical system shown in FIG. 1, with the fourth component inserted into the first component a second amount.

In one embodiment, a selected amount of a material, such as, for example, bone cement is inserted through opening 148 and into lumen 140. Plunger 172 is inserted through opening 148 after the bone cement is inserted into lumen 140, as shown in FIG. 21A. Plunger 172 is moved distally relative to sleeve 42, as shown in FIG. 21B, such that end surface 190 pushes the bone cement in lumen 140 distally. In some embodiments, plunger 172 is moved distally relative to shaft 42 until the bone cement moves out of lumen 140, through portion 120 of channel 116 and cannula 210 such that the bone cement moves out of cannula 210 through fenestrations 212 and/or opening 216. As the bone cement cures, it will bond screw shaft 196 with bone or other tissue.

Figure 22:
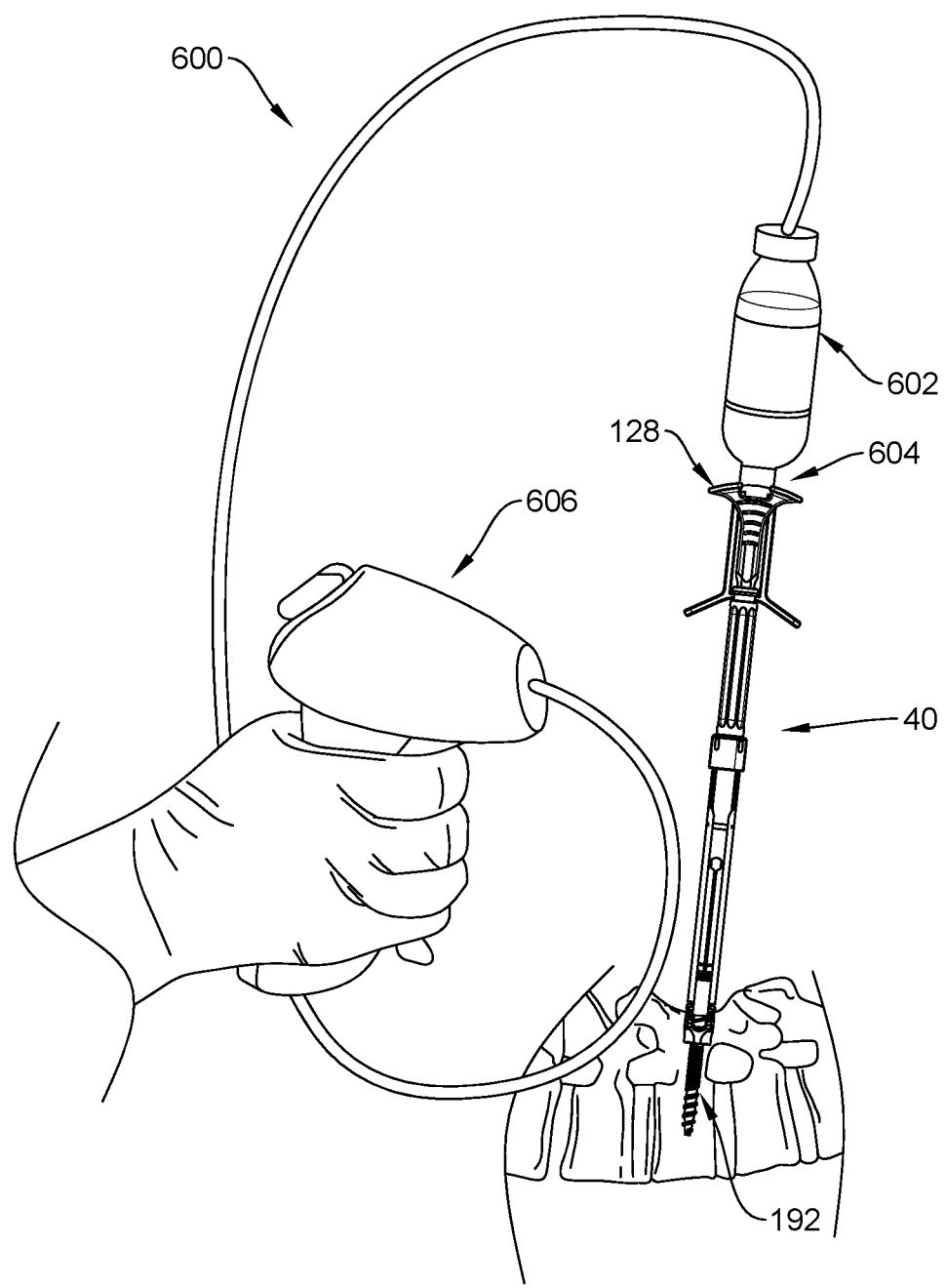
FIG. 22 is a plan view of the embodiment of the surgical system shown in FIG. 1, with a cartridge coupled to the first component.
Figure 23:
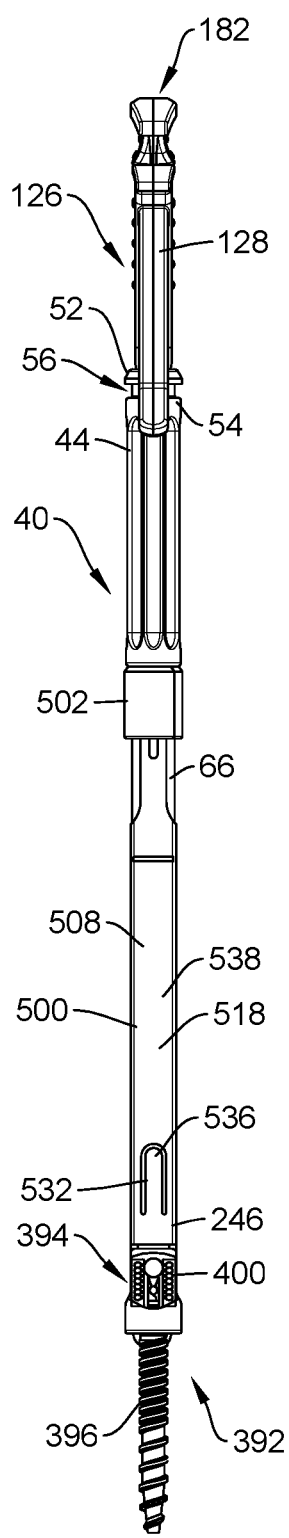
FIG. 23 is a first side view of components of one embodiment of a surgical system in accordance with the principles of the present disclosure.
Figure 24:
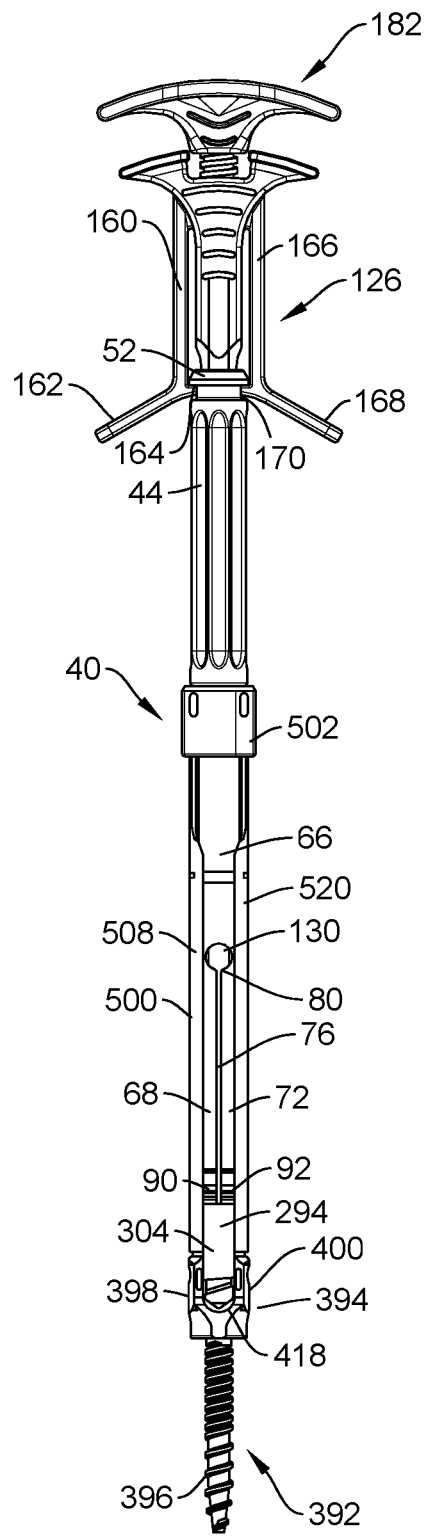
FIG. 24 is a second side view of components of the embodiment of the surgical system shown in FIG. 23.

In one embodiment, a cement delivery system 600 is coupled to delivery device 126 before any bone cement is inserted into lumen 140, as shown in FIG. 22. System 600 includes a cartridge 602 that is connected to handle 128 by a luer lock 604 and a cement delivery gun 606 that is connected to cartridge 602. Threads of luer lock 604 are mated with threaded outer surface 146 to connect cartridge 602 to handle 128. Cartridge 602 is loaded with a bone filler material, such as, for example, bone cement either before or after cartridge 602 is connected to handle 128. An actuator, such as, for example, a trigger handle of cement delivery gun 606 is activated to move the bone cement through lumen 140, portion 120 of channel 116 and cannula 210 such that the bone cement moves out of cannula 210 through fenestrations 212 and/or opening 216. As the bone cement cures, it will bond screw shaft 196 with bone or other tissue.

Upon completion of a surgical procedure, sleeve 42, adapter 94, delivery device 126 and plunger 172 (if used) may be removed from the surgical site. In some embodiments, a spinal construct, such as, for example, a spinal rod is inserted into implant cavity 202 after sleeve 42, adapter 94, delivery device 126 and plunger 172 (if used) are removed from the surgical site and a setscrew is engaged with receiver 194 such that threads on an outer surface of the setscrew engage thread forms 203, 206. The setscrew is rotated relative to receiver 194 until the setscrew engages the rod to fix the rod relative to receiver 194.

In one embodiment, shown in FIGS. 23-32, system 40 includes an adapter 294 in place of adapter 94. It is envisioned that adapter 94 can be replaced with adapter 294, and vice versa, depending upon the requirements of a particular application. Adapter 294 is similar to adapter 94 and is configured to be removably coupled to sleeve 42. Adapter 294 extends along a longitudinal axis A6 between a proximal portion 296 and an opposite distal portion 298. Portion 296 includes a spherical component, such as, for example, an arcuate circumferential shoulder 300 that extends from a body 302 of adapter 294. Adapter 294 includes a circumferential recess 303 between body 302 and shoulder 300. Shoulder 300 has a maximum diameter D4 that is greater than diameter D1 between distal inner surface 69 and distal inner surface 73 when sleeve 42 is in the non-expanded configuration. Diameter D4 is less than second diameter D2 between distal inner surface 69 and distal inner surface 73 when sleeve 42 is in the expanded configuration. In some embodiments, all or only a portion of shoulder 300 may be variously configured and dimensioned, such as, for example, planar, concave, polygonal, irregular, uniform, non-uniform, staggered, tapered, consistent or variable, depending on the requirements of a particular application. In some embodiments, axis A1 is coaxial with axis A6 when adapter 294 is coupled to sleeve 42.

To connect adapter 294 with sleeve 42, a force is applied to leg 68 and/or leg 72 to move leg 68 away from leg 72 such that sleeve 42 moves from the non-expanded configuration to the expanded configuration. In some embodiments, the force that is applied to leg 68 and/or leg 72 to move leg 68 away from leg 72 is provided by shoulder 300. That is, as shoulder 300 moves proximally relative to sleeve 42 to engage surfaces 69, 73, shoulder 300 moves leg 68 away from leg 72, or vice versa, to move sleeve 42 from the non-expanded configuration to the expanded configuration. As sleeve 42 moves from the non-expanded configuration to the expanded configuration, the diameter between distal inner surface 69 and distal inner surface 73 increases from diameter D1 to diameter D2. Since diameter D2 is greater than D4, shoulder 300 is able to be moved proximally passed distal inner surfaces 69,73 and into passageway 50. The force that was applied to leg 68 and/or leg 72 is removed to allow sleeve 42 to move from the expanded configuration to the non-expanded configuration. In some embodiments, removing the force that was applied to leg 68 and/or leg 72 comprises moving shoulder 300 passed distal inner surfaces 69,73 and into passageway 50. Because diameter D4 is less than diameter D1, sleeve 42 prevents adapter 294 from being removed from sleeve 42 when shoulder 300 is positioned within passageway 50. That is, sleeve 42 would have to be moved from the non-expanded configuration to the expanded configuration to remove adapter 294 from sleeve 42 when shoulder 300 is positioned within passageway 50. In some embodiments, surfaces 69, 73 directly engage an outer surface of body 302 and/or an outer surface of shoulder 300 directly engages inner surface 48 when shoulder 300 is positioned within passageway 50 and sleeve 42 is in the non-expanded configuration to provide a clamping force that fixes adapter 294 relative to sleeve 42.

Figure 29:
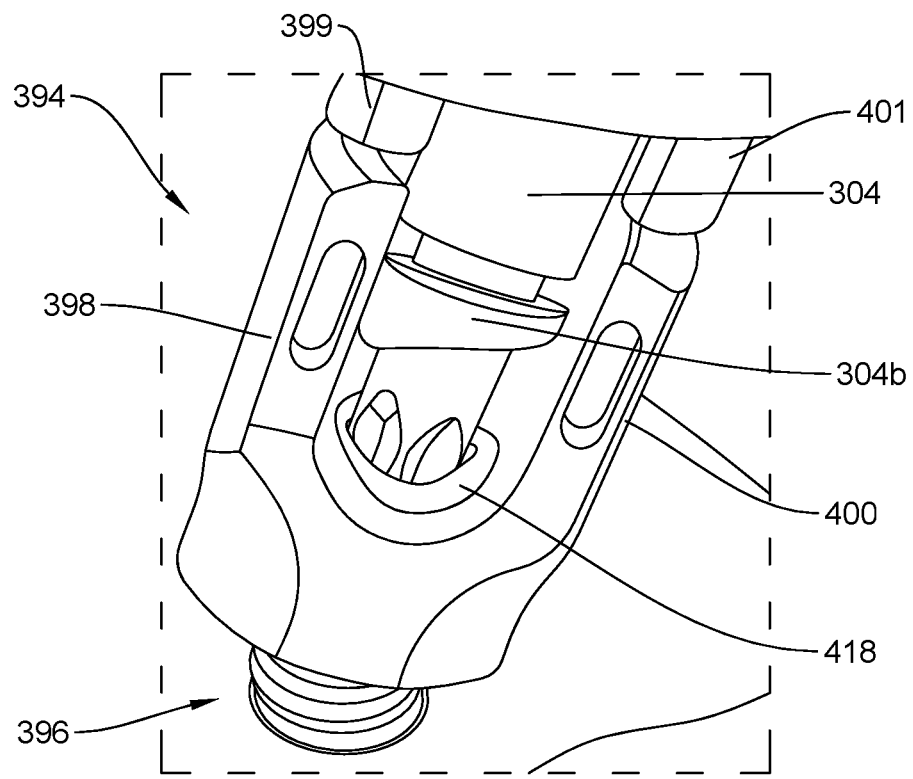
FIG. 29 is a first perspective view of components of the embodiment of the surgical system shown in FIG. 23.
Figure 30:
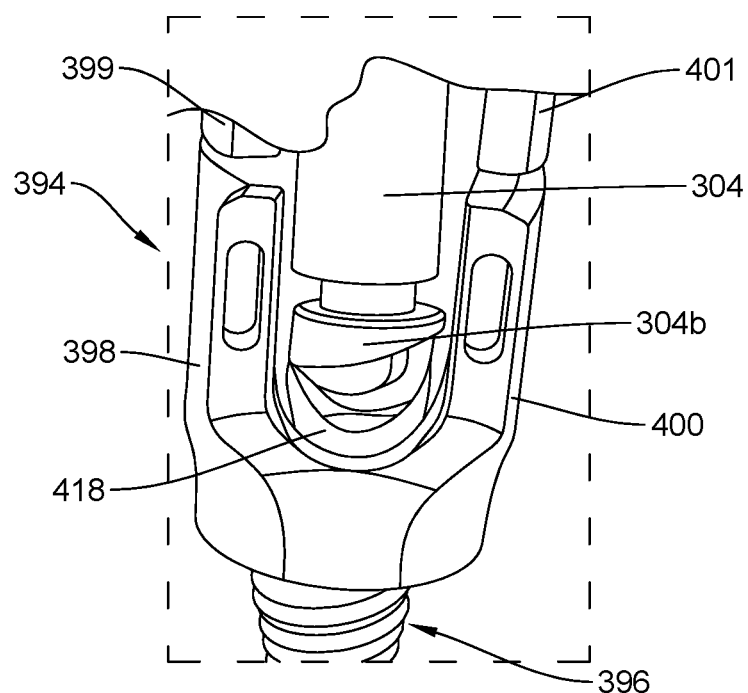
FIG. 30 is a second perspective view of components of the embodiment of the surgical system shown in FIG. 23.

Adapter 294 includes a first flange 304 extending from a first side 306 of body 302 and a second flange 308 extending from an opposite second side 310 of body 302. A top surface 304a of flange 304 and a top surface 308a of flange 308 each extend perpendicular to axis A6. In some embodiments, a side portion 304b of flange 304 and a side portion 308b of flange 308 each have a helical configuration, as shown in FIGS. 29 and 30 for example, to ensure the proper orientation of a tip 312 of adapter 294 when adapter 294 is assembled with a component of system 40, such as, for example, a bone fastener 392, as discussed herein. For example, the helical configuration of flanges 304, 308 provides a helical sweep that helps reorient adapter 294 as adapter 294 is coupled to bone fastener 392 by converting a downward force into a twist, as discussed herein. Tip 312 defines a drive portion configured for disposal within a component of system 40, such as, for example, within a socket 406 of a screw shaft 396 of bone fastener 392. In some embodiments, socket 406 is cylindrical in shape. In some embodiments, surface 304a and/or surface 308a may be disposed at alternate orientations, relative to axis A6, such as, for example, transverse, perpendicular and/or other angular orientations such as acute or obtuse, co-axial and/or may be offset or staggered. In some embodiments, portion 304b and/or portion 308b may be variously configured and dimensioned, such as, for example, planar, concave, polygonal, irregular, uniform, non-uniform, staggered, tapered, consistent or variable, depending on the requirements of a particular application. In some embodiments, the drive portion of tip 312 may include a square, triangular, polygonal, star or hexalobe cross sectional configuration configured engage a correspondingly shaped portion of the component. In some embodiments, the drive portion of tip 312 has a conical shape that ensures that tip 312 will be coaxial with screw shaft 396 when tip 312 is inserted into socket 406, as discussed herein. That is, the conical shape of tip 312 reduces the chance that tip 312 will be not be coaxial with screw shaft 396 when tip 312 is inserted into socket 406. In some embodiments, bone fastener 392 is the same or similar to one or more of the bone fasteners disclosed in U.S. patent Ser. No. 15/415,574, filed Jan. 25, 2017, which is incorporated herein by reference, in its entirely. In some embodiments, bone fastener 392 is the same or similar to one or more of the bone fasteners disclosed in U.S. patent Ser. No. 15/492,867, filed Apr. 20, 2017, which is incorporated herein by reference, in its entirely.

Adapter 294 includes an inner surface 314 defining a channel 316 that extends through the entire length of adapter 294. Channel 316 extends parallel to axis A6. In some embodiments, channel 316 is coaxial with axes A1, A6 when adapter 294 is coupled to sleeve 42. Channel 316 is in communication with passageway 50 when shoulder 310 is positioned in passageway 50. In some embodiments, channel 316 includes a tapered section 318 and a cylindrical section 320 that extends from tapered section 318. Section 320 has a maximum diameter that is greater than a maximum diameter of section 318. Section 318 and section 320 are configured to match the configuration of a tip of delivery device 126 when the tip of delivery device 126 is positioned within section 318 and section 320 to inject a material into channel 316. In some embodiments, section 318 and/or section 320 may have various cross section configurations, such as, for example, oval, oblong, triangular, rectangular, square, polygonal, irregular, uniform, non-uniform, variable, tubular and/or tapered.

Bone fastener 392 includes a head, such as, for example, an implant receiver 394 and a shank, such as, for example, a screw shaft 396 that is coupled to receiver 394 and defines a longitudinal axis A7. Implant receiver 394 includes a pair of spaced apart arms 398, 400 that define an implant cavity 402 therebetween configured for disposal of a spinal construct, such as, for example, a spinal rod. Arms 398, 400 each extend parallel to one another. In some embodiments, arm 398 and/or arm 400 may be disposed at alternate orientations, such as, for example, transverse, perpendicular and/or other angular orientations such as acute or obtuse, coaxial and/or may be offset or staggered. Arms 398, 400 each include an arcuate outer surface extending between a pair of side surfaces. At least one of the outer surfaces and the side surfaces of arms 398, 400 have at least one recess or cavity therein configured to receive an insertion tool, compression instrument and/or instruments for inserting and tensioning bone fastener 392.

Arm 398 includes a break away tab 399 that is frangibly connected to arm 398 such that manipulation of tab 399 relative to arm 398 can fracture and separate tab 399 from arm 398 at a predetermined force and/or torque limit, as described herein. In some embodiments, as force and/or torque is applied to tab 399 and resistance increases, for example, the predetermined torque and force limit is approached. Arm 400 includes a break away tab 401 that is frangibly connected to arm 400 such that manipulation of tab 401 relative to arm 400 can fracture and separate tab 401 from arm 400 at a predetermined force and/or torque limit, as described herein. In some embodiments, as force and/or torque is applied to tab 401 and resistance increases, for example, the predetermined torque and force limit is approached.

In some embodiments, tabs 399, 401 can fracture and separate at a predetermined force or torque limit, which may be in a range of approximately 2 Newton meters (N-m) to 8 Nm. In some embodiments, tabs 399, 401 and arms 398, 400 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 94, 96 from arms 88, 90.

Cavity 402 is substantially U-shaped. In some embodiments, all or only a portion of cavity 402 may have alternate cross section configurations, such as, for example, closed, V-shaped, W-shaped, oval, oblong triangular, square, polygonal, irregular, uniform, non-uniform, offset, staggered, and/or tapered. Implant receiver 394 includes thread forms 403, 405 configured for engagement with a coupling member, such as, for example, a setscrew to retain a spinal rod within cavity 402. Thread forms 403, 405 also define a mating element configured to engage the mating element of sleeve 42 that includes threaded portions 90, 92 to couple sleeve 42 to implant receiver 394, as discussed herein. In some embodiments, the inner surface of implant receiver 394 may be disposed with the coupling member and/or sleeve 42 in alternate fixation configurations, such as, for example, friction fit, pressure fit, locking protrusion/recess, locking keyway and/or adhesive. In some embodiments, all or only a portion of the inner surface of implant receiver 394 may have alternate surface configurations to enhance engagement with a spinal rod, a setscrew and/or sleeve 42, such as, for example, rough, arcuate, undulating, mesh, porous, semi-porous, dimpled and/or textured. In some embodiments, implant receiver 394 may include alternate configurations, such as, for example, closed, open and/or side access.

Implant receiver 394 defines a cavity 404 configured for disposal of a head of screw shaft 396, as described herein. Screw shaft 396 includes a tool engaging portion, such as, for example, socket 406 configured to engage the drive portion of tip 312. Socket 406 is coaxial with axis A7. In some embodiments, tip 312 is rotatable relative to screw shaft 396 when tip 312 is disposed in socket 406. In some embodiments, tip 312 is configured for disposal in socket 406 such that tip 312 engages a surface of screw shaft 396 that defines socket 406 and rotation of adapter 294 also rotates screw shaft 396. In some embodiments, tip 312 includes a plurality of spaced apart lobes that are the same or similar to lobes 113 and are each configured for disposal in one of a plurality of spaced apart lobes of socket 406 that are the same or similar to lobes 209 to prevent rotation of tip 312 relative to screw shaft 396 when tip 312 is disposed in socket 406 such that rotation of adapter 294 also rotates screw shaft 396.

Screw shaft 396 includes an outer surface having an external thread form. In some embodiments, the external thread form may include a single thread turn or a plurality of discrete threads. Screw shaft 396 includes an inner surface 408 defining a cannula 410 that extends the entire length of screw shaft 396. Cannula 410 is coaxial with axis A7. When the drive portion of tip 312 engages tool engaging portion 406, channel 316 is in communication and coaxial with cannula 410. In some embodiments, screw shaft 396 includes one or a plurality of openings or fenestrations that are the same or similar to fenestrations 212 that each extend through surface 408 and an opposite outer surface of screw shaft 396 such that a material, such as, for example, bone cement disposed in cannula 410 can exit cannula 410 through one of the fenestrations and/or through an opening 416 in a distal end of screw shaft 396.

In some embodiments, implant receiver 394 is manually engageable with screw shaft 396 in a non-instrumented assembly, as described herein. In some embodiments, manual engagement and/or non-instrumented assembly of implant receiver 394 and screw shaft 396 includes coupling without use of separate and/or independent instrumentation engaged with the components to effect assembly. In some embodiments, manual engagement and/or non-instrumented assembly includes a practitioner, surgeon and/or medical staff grasping implant receiver 394 and screw shaft 396 and forcibly assembling the components. In some embodiments, manual engagement and/or non-instrumented assembly includes a practitioner, surgeon and/or medical staff grasping implant receiver 394 and screw shaft 396 and forcibly snap fitting the components together, as described herein. In some embodiments, manual engagement and/or non-instrumented assembly includes a practitioner, surgeon and/or medical staff grasping implant receiver 394 and screw shaft 396 and forcibly pop fitting the components together and/or pop fitting implant receiver 394 onto screw shaft 396, as described herein. In some embodiments, a force in a range of 2-50 N is required to manually engage implant receiver 394 and screw shaft 396 and forcibly assemble the components. In some embodiments, a force in a range of 5-10 N is required to manually engage implant receiver 394 and screw shaft 396 and forcibly assemble the components.

In some embodiments, implant receiver 394 is connectable with screw shaft 396 such that screw shaft 396 is pivotable and/or rotatable relative to implant receiver 394 in a plurality of planes. In some embodiments, implant receiver 394 is connectable with screw shaft 396 to include various configurations, such as, for example, a posted screw, a pedicle screw, a bolt, a bone screw for a lateral plate, an interbody screw, a uni-axial screw (UAS), a fixed angle screw (FAS), a multi-axial screw (MAS), a side loading screw, a sagittal adjusting screw (SAS), a transverse sagittal adjusting screw (TSAS), an awl tip (ATS), a dual rod multi-axial screw (DRMAS), midline lumbar fusion screw and/or a sacral bone screw.

Figure 30A:
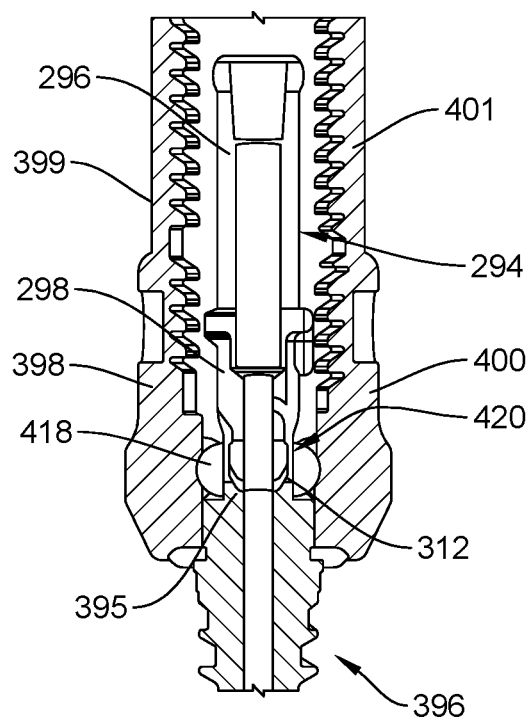
FIG. 30A is a side, cross-sectional view of components of the embodiment of the surgical system shown in FIG. 23.
Figure 30B:
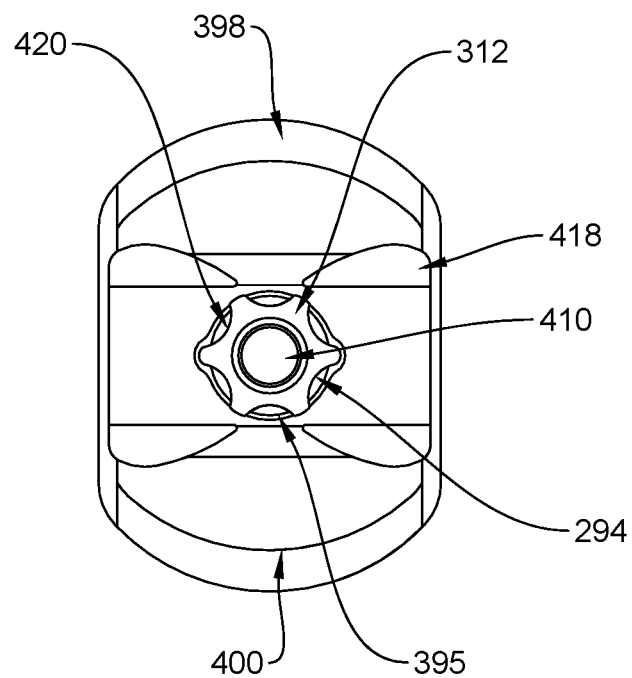
FIG. 30B is a top, cross-sectional view of components of the embodiment of the surgical system shown in FIG. 23.
Figures 31, 32:
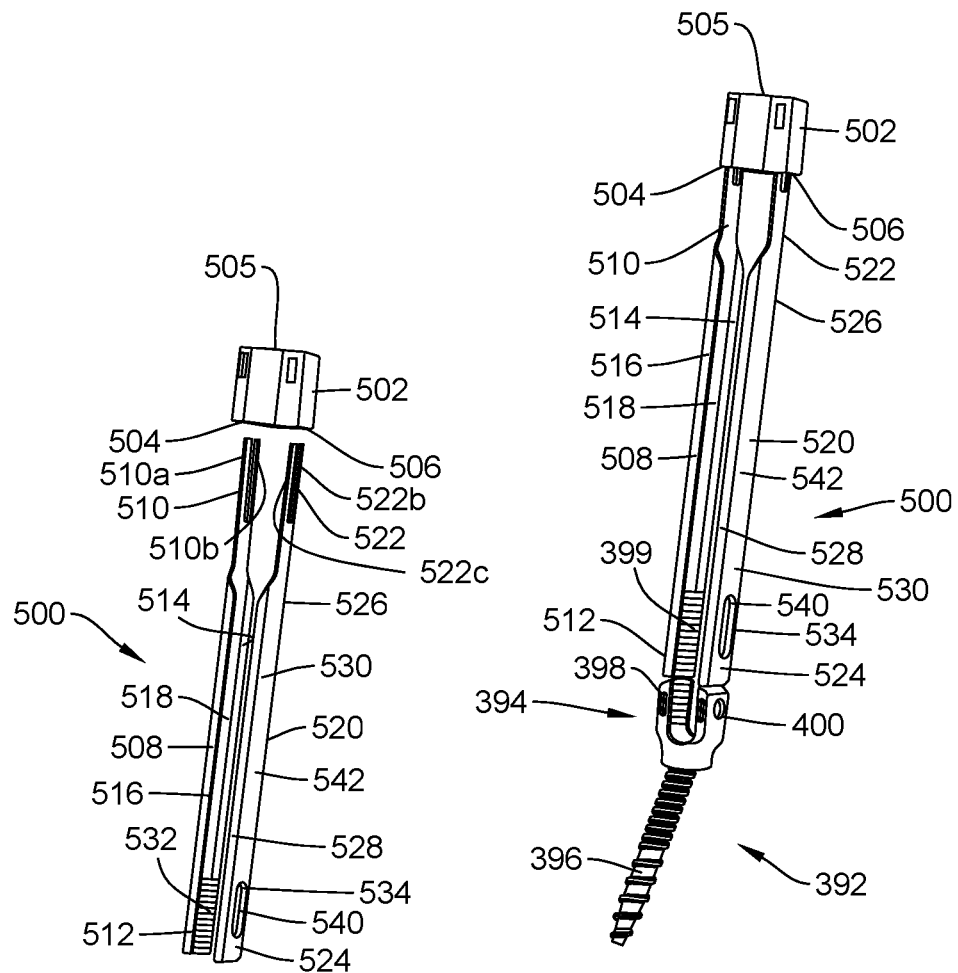
FIG. 31 is a perspective view of a third component of the embodiment of the surgical system shown in FIG. 23.
FIG. 32 is a perspective view of the third component of the embodiment of the surgical system shown in FIG. 23 coupled to the second component of the embodiment of the surgical system shown in FIG. 23.
Figure 33:
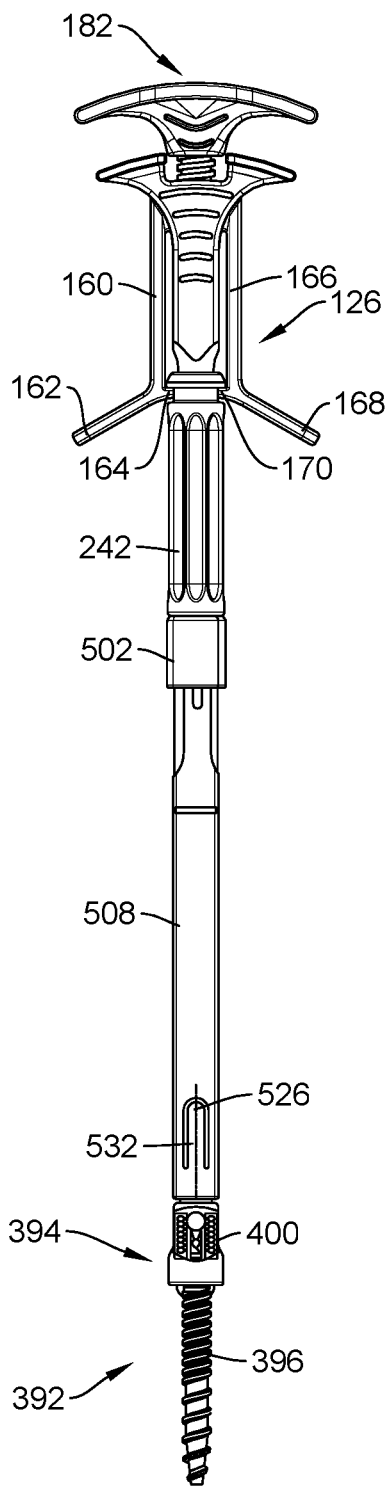
FIG. 33 is a first side view of components of one embodiment of a surgical system in accordance with the principles of the present disclosure.
Figure 34:
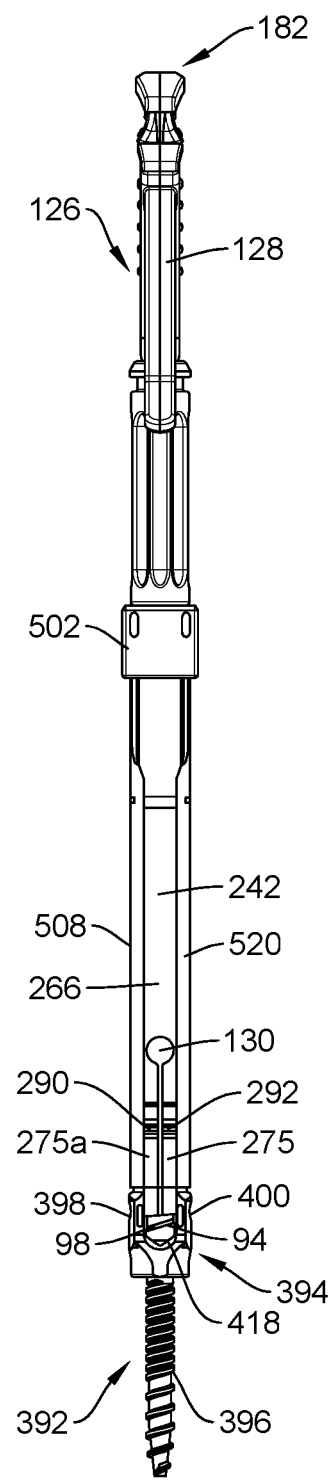
FIG. 34 is a second side view of components of the embodiment of the surgical system shown in FIG. 33.

Bone fastener 392 includes a saddle 418 configured for disposal in cavity 402 such that a bottom surface of saddle 418 directly engages the head of screw shaft 396. In some embodiments, saddle 418 is movable relative to receiver 394 to provide vertebral body control with accommodation of rod seating and allow a medical practitioner the ability to position bone fastener 392 in the natural kyphotic (outward) and lordoditc (inward) curve of the spine. Saddle 418 includes an aperture 420 that extends through a thickness of saddle 418. Aperture 420 is configured for disposal of tip 312 to allow tip 312 to extend through aperture 420 and into socket 406, as shown in FIGS. 30A and 30B, for example. In some embodiments, tip 312 forms a seal with bone fastener 392 as tip 312 passes through saddle 418 and enters socket 406. In some embodiments, aperture 420 is cylindrical in shape. In some embodiments, aperture 420 may have various cross section configurations, such as, for example, circular, oval, oblong, triangular, rectangular, square, polygonal, irregular, uniform, non-uniform, variable, tubular and/or tapered.

Bone fastener 392 includes a band, such as, for example, a ring 424 configured for disposal in a groove 426 of receiver 394 to retain screw shaft 396 with receiver 394. In some embodiments, ring 424 is C-shaped and includes a gap between opposite ends of ring 424. Ring 424 is configured to engage an outer surface of the head of screw shaft 396 and is disposable with groove 426 to prevent axial translation of screw shaft 396 relative to receiver 394 and facilitate rotation of screw shaft 396 relative to receiver 394. In some embodiments, ring 424 is disposed within receiver 394 to enhance a retaining strength of bone fastener 392 and resist and/or prevent shearing of screw shaft 396. In some embodiments, bone fastener 392 is assembled by coupling saddle 418 to the head of screw shaft 396 such that aperture 420 is aligned with socket 406 and inserting the head of screw shaft 396 proximally into cavity 404. Ring 424 is then positioned about screw shaft 396 and screw shaft 396 is moved proximally through cavity 404 and into groove 424 such that ring 424 is seated within groove 426 to prevent the head of screw shaft 396 from moving distally relative to receiver 394.

System 40 includes a component, such as, for example, an extender 500 comprising a collar 502 having a first opening 504 and a second opening 506 that is spaced apart from opening 504. Collar 502 includes an aperture 505 between opening 504 and opening 506 that is configured for disposal of sleeve 42, as discussed herein. A first leg 508 of extender 500 includes a first end 510 configured for disposal in opening 504 and a second end 512 configured to engage implant receiver 394. In particular, leg 508 includes a side wall 514 configured to engage a side surface 399a of tab 399, a side wall 516 configured to engage a side surface 399b of tab 399, and a middle wall 518 configured to engage a wall 399c of tab 399. A second leg 520 of extender 500 includes a first end 522 configured for disposal in opening 506 and a second end 524 configured to engage implant receiver 394. In particular, leg 520 includes a side wall 526 configured to engage a side surface 401a of tab 401, a side wall 528 configured to engage a side surface 401b of tab 401, and a middle wall 530 configured to engage a wall 401c of tab 401.

In some embodiments, end 510 includes a pair of spaced apart tines 510a, 510b and end 522 includes a pair of spaced apart tines 522a, 522b. Tines 510a, 510b are movable between non-compressed configuration in which a distance from an outer surface of tine 510a to an opposite outer surface of tine 510b is greater than a maximum width of opening 504 and a compressed configuration in which the distance from the outer surface of tine 510a to the outer surface of tine 510b is less than the maximum width of opening 504. In some embodiments, tines 510a, 510b are biased to the non-compressed configuration such that tines 510a, 510b will return to the non-compressed configuration from the compressed configuration after a force that is used to move tines 510a, 510b from the non-compressed configuration to the compressed configuration is removed. To insert end 510 in opening 504, tines 510a, 510b are moved from the non-compressed configuration to the compressed configuration by moving tine 510a toward tine 510b and/or moving tine 510b toward tine 510a. After tines 510a, 510b are in the compressed configuration, end 510 is inserted into opening 504. In some embodiments, tines 510a, 510b move away from one another or expand within opening 504 after end 510 is inserted into opening 504 to fix leg 508 with cap 502. Tines 522a, 522b are movable between non-compressed configuration in which a distance from an outer surface of tine 522a to an opposite outer surface of tine 522b is greater than a maximum width of opening 506 and a compressed configuration in which the distance from the outer surface of tine 522a to the outer surface of tine 522b is less than the maximum width of opening 506. In some embodiments, tines 522a, 522b are biased to the non-compressed configuration such that tines 522a, 522b will return to the non-compressed configuration from the compressed configuration after a force that is used to move tines 522a, 522b from the non-compressed configuration to the compressed configuration is removed. To insert end 522 in opening 506, tines 522a, 522b are moved from the non-compressed configuration to the compressed configuration by moving tine 522a toward tine 522b and/or moving tine 522b toward tine 522a. After tines 522a, 522b are in the compressed configuration, end 522 is inserted into opening 506. In some embodiments, tines 522a, 522b move away from one another or expand within opening 506 after end 522 is inserted into opening 506 to fix leg 520 with cap 502.

In some embodiments, leg 508 includes a mating element, such as, for example, a spring tab 532 and leg 520 includes a mating element, such as, for example, a spring tab 534. Spring tab 532 is configured to deflect relative to wall 518 and spring tab 534 is configured to deflect relative to wall 530. Spring tab 532 is configured to deflect relative to wall 518 and spring tab 534 is configured to deflect relative to wall 530. Spring tab 532 is movable between a non-locking configuration in which an outer surface 536 of spring tab 532 is flush with an outer surface 538 of wall 518 and a locking configuration in which outer surface 536 is positioned inwardly of outer surface 538. In some embodiments, spring tab 532 is biased to the locking configuration such that spring tab 532 will return to the locking configuration after a force that is used to move spring tab 532 from the non-locking configuration to the locking configuration is removed. Likewise, spring tab 534 is movable between a non-locking configuration in which an outer surface 540 of spring tab 534 is flush with an outer surface 542 of wall 530 and a locking configuration in which outer surface 540 is positioned inwardly of outer surface 542. In some embodiments, spring tab 534 is biased to the locking configuration such that spring tab 534 will return to the locking configuration after a force that is used to move spring tab 534 from the non-locking configuration to the locking configuration is removed. In some embodiments, a portion of spring tab 532 is positioned in an aperture 544 in tab 399 when spring tab 532 is in the locking configuration and is spaced apart from aperture 544 when spring tab 532 is in the non-locking configuration. In some embodiments, the portion of spring tab 532 is a projection that extends from an inner surface of spring tab 532. In some embodiments, the projection has a size and shape that matches that of aperture 544 such that the projection does not move within aperture 544. In some embodiments, a portion of spring tab 534 is positioned in an aperture 546 in tab 401 when spring tab 534 is in the locking configuration and is spaced apart from aperture 546 when spring tab 534 is in the non-locking configuration. In some embodiments, the portion of spring tab 534 is a projection that extends from an inner surface of spring tab 534. In some embodiments, the projection has a size and shape that matches that of aperture 546 such that the projection does not move within aperture 546.

Figure 25:
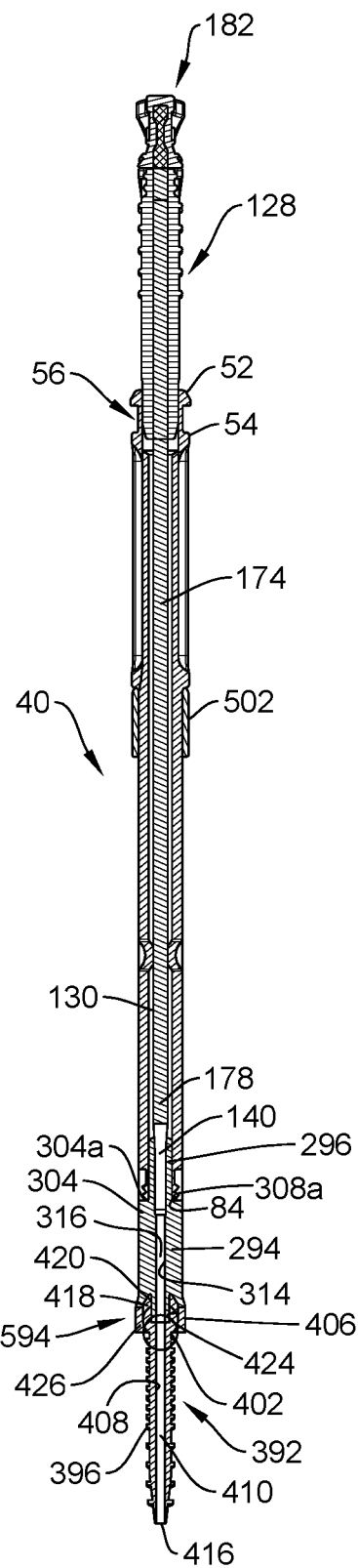
FIG. 25 is a first side, cross-sectional view of components of the embodiment of the surgical system shown in FIG. 23.
Figure 26:
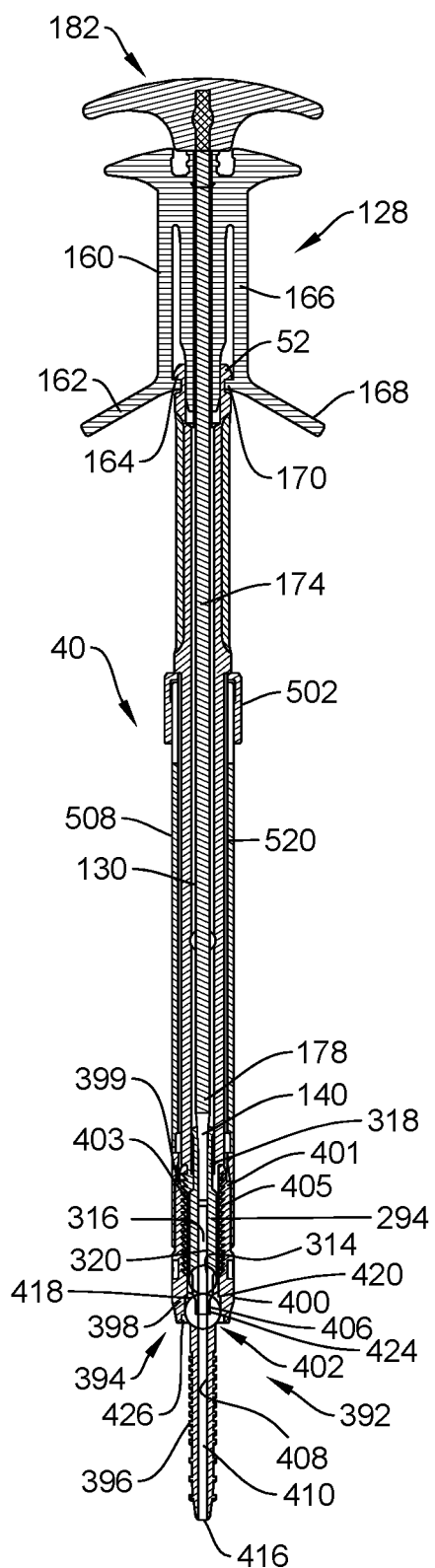
FIG. 26 is a second, cross-sectional view of components of the embodiment of the surgical system shown in FIG. 23.
Figure 27:
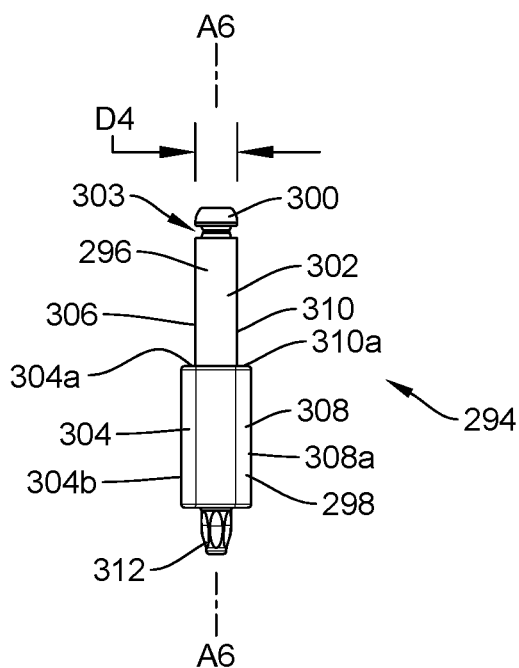
FIG. 27 is a side view of a first component of the embodiment of the surgical system shown in FIG. 23.
Figure 28:
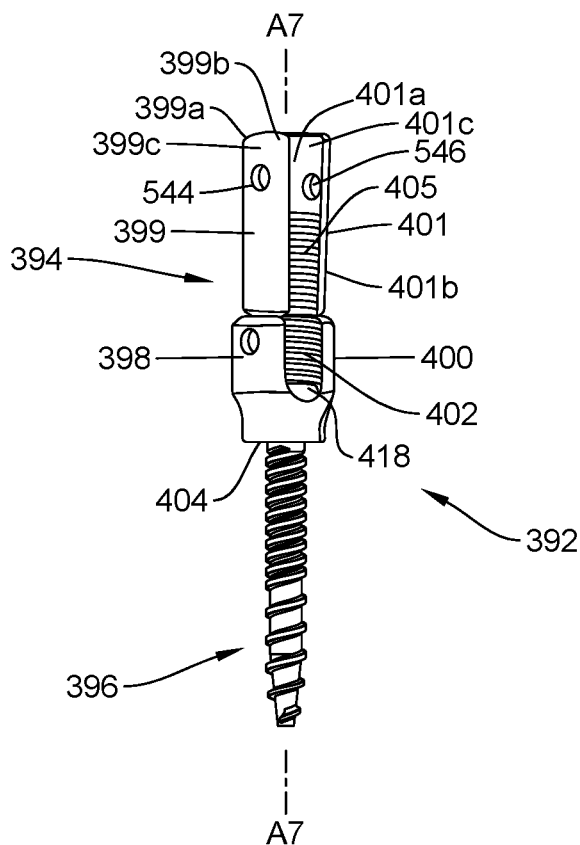
FIG. 28 is a side view of a second component of the embodiment of the surgical system shown in FIG. 23.

In assembly, operation and use, access to the surgical site is obtained and the particular surgical procedure is performed. The components of surgical system 40 are employed to augment the surgical treatment. For example, adapter 294 is coupled to sleeve 42, as discussed herein, such that end surface 84 directly engages top surface 304a of flange 304 and top surface 308a of flange 308 and channel 316 is in communication with passageway 50, as shown in FIGS. 25 and 26.

Bone fastener 392 is assembled in the manner discussed herein. Screw shaft 396 is selectively positioned adjacent tissue, such as, for example, bone. In some embodiments, a distal tip of screw shaft 396 is inserted into a pilot hole that was formed in the bone. A drive bit of a driver, such as, for example, a screwdriver is inserted into tool engaging portion 406 of screw shaft 396. The screwdriver is then rotated to rotate screw shaft 396 to translate screw shaft 396 relative to the bone until screw shaft 396 is inserted a selected amount into the bone for fixation of screw shaft 396 with the bone. Bone fastener 392 is connected with extender 500 by positioning leg 508 over tab 399 such that side wall 514 engages side surface 399a of tab 399, side wall 516 engages side surface 399b of tab 399, and middle wall 518 engages wall 399c of tab 399. In some embodiments, leg 508 is positioned over tab 399 such that spring tab 532 moves from the non-locking configuration to the locking configuration, as discussed herein. Leg 520 is positioned over tab 401 such that side wall 526 engages side surface 401a of tab 401, side wall 528 engages side surface 401b of tab 401, and middle wall 530 engages wall 401c of tab 401. In some embodiments, leg 520 is positioned over tab 401 such that spring tab 534 moves from the non-locking configuration to the locking configuration, as discussed herein. End 510 is inserted into opening 504 by moving tines 510a, 510b from the non-compressed configuration to the compressed configuration and inserting tines 510a, 510b into opening 504. End 522 is inserted into opening 506 by moving tines 522a, 522b from the non-compressed configuration to the compressed configuration and inserting tines 522a, 522b into opening 506.

Sleeve 42 and adapter 294 are connected with bone fastener 392 and extender 500 by positioning end 46 through aperture 505 and translating sleeve 42 and adapter 294 distally relative to extender 500 with flanges 304, 308 each positioned between legs 508, 520. Sleeve 42 is translated distally relative to extender 500 until threaded portions 90, 92 are positioned adjacent to thread forms 403, 405. The helical configurations of portions 304b, 308b of flanges 304, 308 maintain the orientation of tip 312 such that channel 316 remains coaxial with passageway 50 as sleeve 42 and adapter 242 are connected with bone fastener 392, as discussed herein. Sleeve 42 is rotated relative to receiver 394 such that threaded portions 90, 92 mate with thread forms 403, 405 to fix sleeve 42 and adapter 294 relative to receiver 394. Sleeve 42 is rotated relative to receiver 394 until tip 312 extends through aperture 420 and tip 312 is disposed in socket 406 such that the drive portion of tip 312 engages the tool engagement portion of socket 406 to prevent rotation of tip 312 relative to screw shaft 396, tip 312 forms a seal with socket 406, and channel 316 is in communication with cannula 410. In some embodiments, the seal formed by tip 312 and socket 406 ensures that any material that moves out of channel 316 will move directly into cannula 410 and will not exude into socket 406.

In one embodiment, a selected amount of a material, such as, for example, bone cement is inserted through opening 148 and into lumen 140. Plunger 172 is then inserted through opening 148, after the bone cement is inserted into lumen 140. Plunger 172 is moved distally relative to sleeve 42 such that end surface 190 pushes the bone cement in lumen 140 distally. In some embodiments, plunger 172 is moved distally relative to shaft 42 until the bone cement moves out of lumen 140, through channel 316 and cannula 410 such that the bone cement moves out of cannula 410 through opening 416. As the bone cement cures, it will bond screw shaft 396 with bone or other tissue.

In one embodiment, cement delivery system 600 is coupled to delivery device 126 before any bone cement is inserted into lumen 140. Threads of luer lock 604 are mated with threaded outer surface 146 to connect cartridge 602 to handle 128. Cartridge 602 is loaded with a bone filler material, such as, for example, bone cement either before or after cartridge 602 is connected to handle 128. An actuator, such as, for example, a trigger handle of cement delivery gun 606 is activated to move the bone cement through lumen 140, channel 316 and cannula 410 such that the bone cement moves out of cannula 410 through opening 416. As the bone cement cures, it will bond screw shaft 396 with bone or other tissue.

Upon completion of a surgical procedure, sleeve 42, adapter 294, delivery device 126 and plunger 172 (if used) may be removed from the surgical site. In some embodiments, a spinal construct, such as, for example, a spinal rod is inserted into implant cavity 402 after sleeve 42, adapter 294, delivery device 126 and plunger 172 (if used) are removed from the surgical site and a setscrew is engaged with receiver 394 such that threads on an outer surface of the setscrew engage thread forms 403, 406. The setscrew is rotated relative to receiver 394 until the setscrew engages the rod to fix the rod relative to receiver 394.

In one embodiment, shown in FIGS. 33-38, system 40 includes a sleeve 242 in place of sleeve 42. Sleeve 242 extends along a longitudinal axis A1 between a proximal end 244 and an opposite distal end 246. Sleeve 242 includes an inner surface 248 that defines a passageway 250. In some embodiments, passageway 250 is coaxial with axis A8 and extends the entire length of sleeve 242. That is, passageway 250 extends between and through opposite end surfaces of ends 244, 246 such that a component of system 40 can be inserted through the end surface of end 244 and into passageway and a component of system 40 can be inserted through the end surface of end 246 and into passageway 250. In some embodiments, passageway 250 has a circular diameter. In some embodiments, passageway 250 has a uniform diameter along the entire length of sleeve 242. In some embodiments, passageway 250 may be disposed at alternate orientations, relative to axis A8, such as, for example, transverse, perpendicular and/or other angular orientations such as acute or obtuse, co-axial and/or may be offset or staggered. In some embodiments, passageway 250 may have various cross section configurations, such as, for example, oval, oblong, triangular, rectangular, square, polygonal, irregular, uniform, non-uniform, variable, tubular and/or tapered. In some embodiments, sleeve 242 is configured to be reused and is made from a metal material, such as, for example, stainless steel to provide strength and rigidity to sleeve 242. However, it is envisioned that sleeve 242 can also be made from any of the other materials discussed herein, such as, for example, stainless steel alloys, commercially pure titanium, titanium alloys, Grade 5 titanium, cobalt-chrome alloys.

Figure 37:
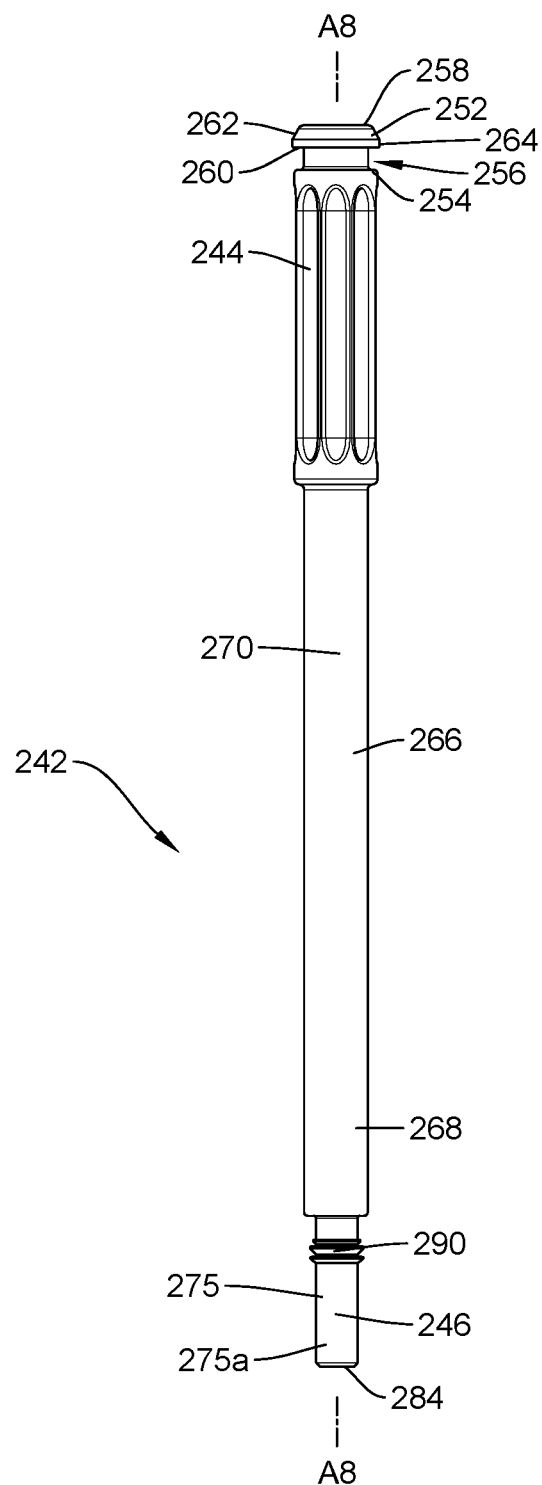
FIG. 37 is a first side view of a first component of the embodiment of the surgical system shown in FIG. 33.
Figure 38:
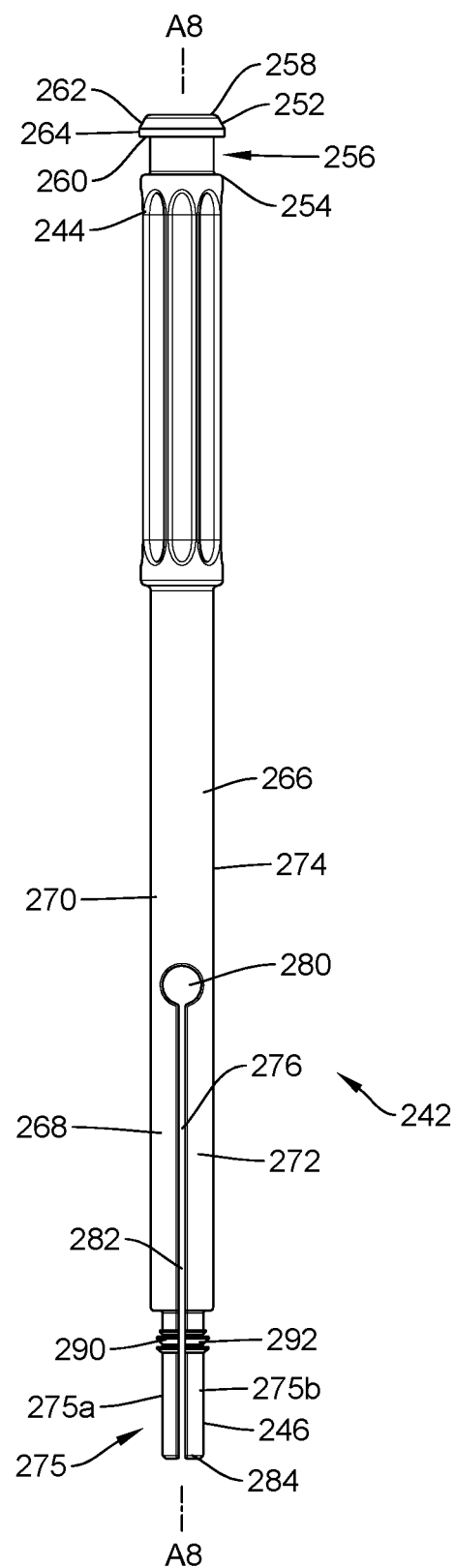
FIG. 38 is a second side view of the first component of the embodiment of the surgical system shown in FIG. 33.

End 244 includes a mating element, such as, for example, a flange 252 configured to connect delivery device 126 with sleeve 242, as discussed herein. Flange 252 is spaced apart from a flange 254 by an undercut, such as, for example, a recess 256. Flange 252 includes opposite surfaces 258, 260 that each extend perpendicular to axis A8 and surfaces 262, 264 that are each positioned between surfaces 258, 260, as best shown in FIG. 37. Surface 258 defines the end surface of end 244. Surface 262 extends transverse to axis A8 and surface 264 extends parallel to axis A8. In some embodiments, surface 258, surface 260, surface 262 and/or surface 264 may be disposed at alternate orientations, relative to longitudinal axis A8, such as, for example, parallel, transverse, perpendicular and/or other angular orientations such as acute or obtuse and/or may be offset or staggered.

Sleeve 242 includes a body 266. End 246 includes a leg 268 extending from a side 270 of body 266 and a leg 272 extending from a side 274 of body 266 such that leg 272 faces leg 268. Legs 268, 272 are separated by a gap 276. Gap 276 includes a substantially circular proximal portion 280 and a linear distal portion 282 that extends through an end surface 284 of end 246. In some embodiments, portion 280 is variously shaped, such as, for example, oval, oblong, triangular, square, polygonal, irregular, uniform, non-uniform, offset, staggered, undulating, arcuate, variable and/or tapered. In some embodiments, portion 282 may be disposed at alternate orientations, relative to axis A8, such as, for example, transverse, perpendicular and/or other angular orientations such as acute or obtuse, co-axial and/or may be offset or staggered.

Gap 276 permits leg 268 move relative to leg 272 to move sleeve 422 between a non-expanded configuration and an expanded configuration to connect a component of system 40, such as, for example, adapter 294 with sleeve 242, as discussed herein. That is, leg 268 is configured to move away from leg 272, or vice versa, to increase the width of portion 282 and move sleeve 242 from the non-expanded configuration to the expanded configuration. In some embodiments, sleeve 242 will remain in the non-expanded configuration unless and until a force is applied to leg 268 and/or leg 272 to move sleeve 242 from the non-expanded configuration to the expanded configuration. In some embodiments, sleeve 242 is resiliently biased to the non-expanded configuration such that sleeve 242 will move from the expanded configuration to the non-expanded configuration after the force that moves sleeve 242 from the non-expanded configuration to the expanded configuration is removed.

In some embodiments, end 246 includes an extrusion 275 extending distally from body 266. Extrusion 275 has a maximum diameter that is less than a maximum diameter of body 266. Extrusion includes a first part 275a that forms a distal end of leg 268 and a second part 275b that forms a distal end of leg 272. Part 275a includes a first threaded portion 290 and part 275b includes a second threaded portion 292. Threaded portions 290, 292 are spaced apart from one another by gap 276 and cooperate to define a mating element configured to engage a mating element of a component of system 40, such as, for example, bone fastener 392 to connect bone fastener 392 with sleeve 242, as discussed herein.

To connect adapter 94 with sleeve 242, a force is applied to leg 268 and/or leg 272 to move leg 268 away from leg 272 such that sleeve 242 moves from the non-expanded configuration to the expanded configuration. In some embodiments, the force that is applied to leg 268 and/or leg 272 to move leg 268 away from leg 272 is provided by shoulder 100. That is, as shoulder 100 moves proximally relative to sleeve 242, shoulder 100 moves leg 268 away from leg 272, or vice versa, to move sleeve 242 from the non-expanded configuration to the expanded configuration. As sleeve 242 moves from the non-expanded configuration to the expanded configuration, the diameter between legs 268, 272 increases to allow shoulder 100 to be moved proximally into passageway 250. The force that was applied to leg 268 and/or leg 272 is removed to allow sleeve 242 to move from the expanded configuration to the non-expanded configuration. In some embodiments, removing the force that was applied to leg 268 and/or leg 272 comprises moving shoulder 100 into passageway 250. Sleeve 42 exerts a clamping force on adapter 94 to prevent adapter 94 from being removed from sleeve 242 when shoulder 100 is positioned within passageway 250. That is, sleeve 242 would have to be moved from the non-expanded configuration to the expanded configuration to remove adapter 94 from sleeve 242 when shoulder 100 is positioned within passageway 250.

Figure 35:
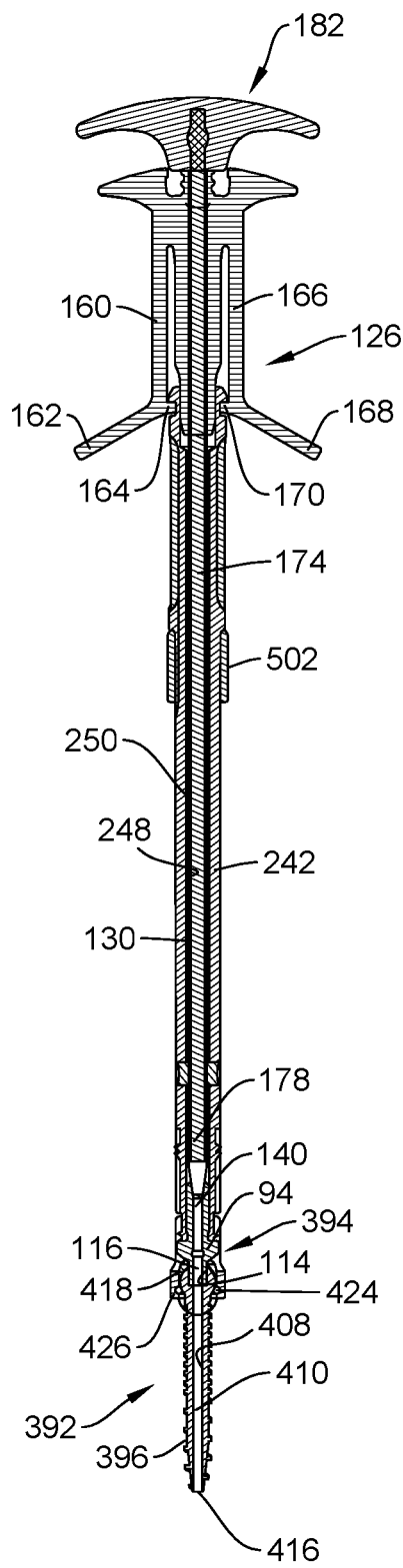
FIG. 35 is a first side, cross-sectional view of components of the embodiment of the surgical system shown in FIG. 33.
Figure 36:
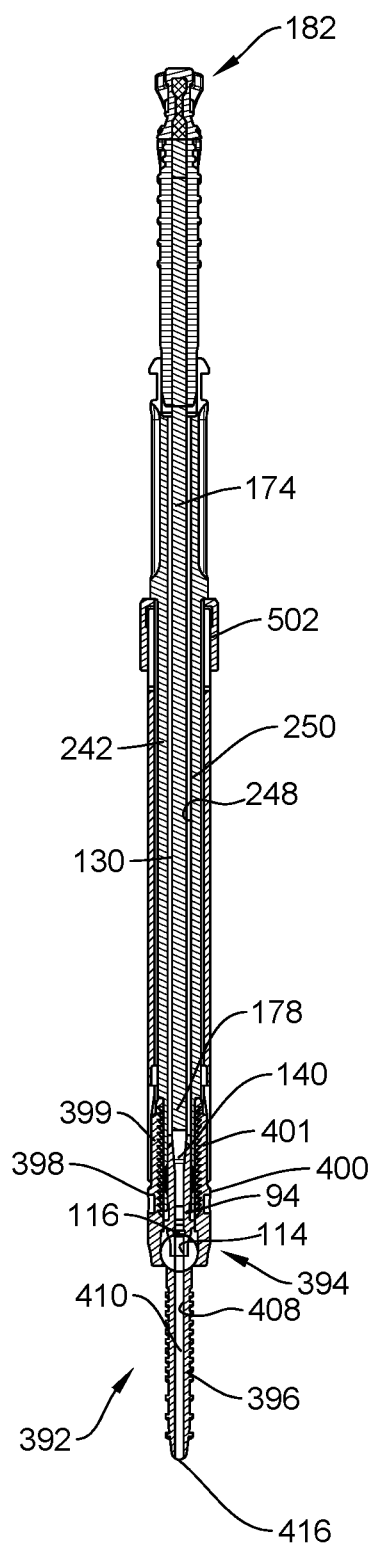
FIG. 36 is a second, cross-sectional view of components of the embodiment of the surgical system shown in FIG. 33.

In assembly, operation and use, access to the surgical site is obtained and the particular surgical procedure is performed. The components of surgical system 40 are employed to augment the surgical treatment. For example, adapter 94 is coupled to sleeve 242, as discussed herein, such that end surface 284 directly engages top surface 104a of flange 104 and top surface 108a of flange 108 and channel 116 is in communication with passageway 250, as shown in FIGS. 35 and 36.

Bone fastener 392 is assembled in the manner discussed herein. Screw shaft 396 is selectively positioned adjacent tissue, such as, for example, bone. In some embodiments, a distal tip of screw shaft 396 is inserted into a pilot hole that was formed in the bone. A tip of a screwdriver is inserted into socket 406. Rotation of the screwdriver rotates screw shaft 396 to drive screw shaft 396 into the bone. Once screw shaft 396 is driven a selected amount into bone, bone fastener 392 is connected with extender 500 by positioning leg 508 over tab 399 such that side wall 514 engages side surface 399a of tab 399, side wall 516 engages side surface 399b of tab 399, and middle wall 518 engages wall 399c of tab 399. In some embodiments, leg 508 is positioned over tab 399 such that spring tab 532 moves from the non-locking configuration to the locking configuration, as discussed herein. Leg 520 is positioned over tab 401 such that side wall 526 engages side surface 401a of tab 401, side wall 528 engages side surface 401b of tab 401, and middle wall 530 engages wall 401c of tab 401. In some embodiments, leg 520 is positioned over tab 401 such that spring tab 534 moves from the non-locking configuration to the locking configuration, as discussed herein. End 510 is inserted into opening 504 by moving tines 510a, 510b from the non-compressed configuration to the compressed configuration and inserting tines 510a, 510b into opening 504. End 522 is inserted into opening 506 by moving tines 522a, 522b from the non-compressed configuration to the compressed configuration and inserting tines 522a, 522b into opening 506.

Sleeve 242 and adapter 94 are connected with bone fastener 392 and extender 500 by positioning end 246 through aperture 505 and translating sleeve 242 and adapter 94 distally relative to extender 500 with flanges 104, 108 each positioned between legs 508, 520. Sleeve 242 is translated distally relative to extender 500 until threaded portions 290, 292 are positioned adjacent to thread forms 403, 405. The helical configurations of portions 104*b*, 108*b* of flanges 104, 108 maintain the orientation of tip 112 such that channel 116 remains coaxial with passageway 250 as sleeve 242 and adapter 42 are connected with bone fastener 392, as discussed herein. Sleeve 242 is rotated relative to receiver 394 such that threaded portions 290, 292 mate with thread forms 403, 405 to fix sleeve 242 and adapter 94 relative to receiver 394. Sleeve 242 is rotated relative to receiver 394 until tip 112 extends through aperture 420 and tip 112 is disposed in socket 406 such that the drive portion of tip 112 engages the tool engagement portion of socket 406 to prevent rotation of tip 112 relative to screw shaft 396, tip 112 forms a seal with socket 406, and channel 116 is in communication with cannula 410. In some embodiments, the seal formed by tip 112 and socket 406 ensures that any material that moves out of channel 116 will move directly into cannula 410 and will not exude into socket 406.

Delivery device 126 is coupled with sleeve 242 by inserting shaft 130 into passageway 250 and moving shaft 130 distally within passageway 250 until portion 136 is disposed in channel 116 such that lumen 140 is in communication with channel 116 and shaft 130 creates a fluid-tight seal with adapter 94, as discussed herein.

In one embodiment, a selected amount of a material, such as, for example, bone cement is inserted through opening 148 and into lumen 140. Plunger 172 is then inserted through opening 148. Plunger 172 is moved distally relative to sleeve 242 such that end surface 190 pushes the bone cement in lumen 140 distally. In some embodiments, plunger 172 is moved distally relative to shaft 242 until the bone cement moves out of lumen 140, through channel 116 and cannula 410 such that the bone cement moves out of cannula 410 through opening 416. As the bone cement cures, it will bond screw shaft 396 with bone or other tissue.

In one embodiment, cement delivery system 600 is coupled to delivery device 126 before any bone cement is inserted into lumen 140. Threads of luer lock 604 are mated with threaded outer surface 146 to connect cartridge 602 to handle 128. Cartridge 602 is loaded with a bone filler material, such as, for example, bone cement either before or after cartridge 602 is connected to handle 128. An actuator, such as, for example, a trigger handle of cement delivery gun 606 is activated to move the bone cement through lumen 140, channel 116 and cannula 410 such that the bone cement moves out of cannula 410 through opening 416. As the bone cement cures, it will bond screw shaft 396 with bone or other tissue.

Upon completion of a surgical procedure, sleeve 242, adapter 94, delivery device 126 and plunger 172 (if used) may be removed from the surgical site. In some embodiments, a spinal construct, such as, for example, a spinal rod is inserted into implant cavity 402 after sleeve 242, adapter 94, delivery device 126 and plunger 172 (if used) are removed from the surgical site and a setscrew is engaged with receiver 394 such that threads on an outer surface of the setscrew engage thread forms 403, 406. The setscrew is rotated relative to receiver 394 until the setscrew engages the rod to fix the rod relative to receiver 394.

It will be understood that various modifications may be made to the embodiments disclosed herein. Therefore, the above description should not be construed as limiting, but merely as exemplification of the various embodiments. Those skilled in the art will envision other modifications within the scope of the claims appended hereto.

What is claimed is:

1. A surgical system comprising:
    a sleeve comprising a proximal end including a first mating element and a distal end including a second mating element, the sleeve defining a passageway;
    an adapter removably coupled to the sleeve, the adapter defining a channel and comprising a distal portion and a proximal portion, the proximal portion being positioned in the passageway;
    a delivery device comprising a handle and a shaft, a distal end of the shaft being positioned in the channel, the handle comprising a third mating element configured to engage the first mating element to connect the delivery device to the sleeve, the shaft defining a lumen in communication with the channel;
    a bone fastener including a head and a shank defining a cannula, the head comprising a fourth mating element configured to engage the second mating element to connect the bone fastener to the sleeve, the distal portion being positioned in the shank such that the channel is in communication with the cannula; and
    a plunger movably disposed in the lumen and configured to move a material through the lumen and the channel and into the cannula.

2. The surgical system recited in claim 1, wherein engagement of the first mating element with the second mating element prevents the delivery device from moving proximally relative to the sleeve.

3. The surgical system recited in claim 1, wherein the handle comprises a body, the first mating element comprises a flange, and the third mating element comprises a wing extending from the body in a cantilevered configuration.

4. The surgical system recited in claim 1, wherein the handle comprises a body having a first side an opposite second side, the first mating element comprises a flange, and the third mating element comprises a first wing, extending from the first side in a cantilevered configuration, and a second wing extending from the second side in a cantilevered configuration.

5. The surgical system recited in claim 4, wherein:
    the first wing comprises a first extension extending from the first side and a first tab extending from the first extension;
    the second wing comprises a second extension extending from the second side and a second tab extending from the second extension;
    the first and second extensions each extend parallel to a longitudinal axis defined by the sleeve and the first and second tabs each extend perpendicular to the longitudinal axis; and
    the first and second tabs engage the flange to secure the delivery device to the sleeve.

6. The surgical system recited in claim 1, wherein the second mating element comprises an outer thread and the fourth mating element comprises an inner thread.

7. The surgical system recited in claim 1, wherein the distal portion comprises a drive tip disposed in a socket of the shank such that rotation of the adapter rotates the shank.

8. The surgical system recited in claim 1, wherein the bone fastener comprises a saddle engaged with the head, the saddle comprising an aperture, the distal portion fitting within the aperture to create a seal between the adapter and the bone fastener.

9. The surgical system recited in claim 8, wherein:
    the saddle includes a proximal end and a distal end, the aperture being tapered from the proximal end of the saddle to the distal end of the saddle; and the distal portion is tapered toward an end surface of the distal portion.

10. The surgical system recited in claim 1, wherein the sleeve comprises a body, a first leg extending from a first side of the body and a second leg extending from a second side of the body, the legs being separated by a gap, the proximal portion being positioned between the legs.

11. The surgical system recited in claim 10, wherein the legs are resiliently biased toward one another.

12. The surgical system recited in claim 1, wherein the sleeve is movable between an unexpanded configuration in which the passageway has a first diameter and an expanded configuration in which the passageway has a second diameter, the second diameter being greater than the first diameter, the proximal portion having a maximum diameter greater than the first diameter and less than the second diameter.

13. The surgical system recited in claim 1, wherein the shank comprises a fenestration in communication with the cannula.

14. The surgical system recited in claim 1, wherein the adapter comprises a body, a first flange extending from a first side of the body and a second flange extending from the second side of the body, at least one of the first flange and the second flange having a helical configuration.

15. A surgical method comprising:
connecting an adapter with a sleeve such that a channel of the adapter is in communication with a passageway of the sleeve;
engaging a first mating element of the sleeve with a second mating element of a bone fastener to connect the bone fastener with the sleeve such that the channel is in communication with a cannula of the bone fastener;
engaging a third mating element of the sleeve with a fourth mating element of a delivery device to connect the delivery device with the sleeve such that a lumen of the delivery device is in communication with the channel;
inserting a material into the lumen; and
inserting a plunger into the lumen such that the plunger moves the material through the lumen and the channel and into the cannula.

16. The surgical method recited in claim 15, further comprising:
removing the plunger from the lumen;
disengaging the third mating element from the fourth mating element;
disengaging the first mating element from the second mating element;
disconnecting the adapter from the sleeve;
connecting a second adapter with the sleeve such that a second channel of the second adapter is in communication with the passageway;
engaging the first mating element with a fifth mating element of a second bone fastener to connect the second bone fastener with the sleeve such that the second channel is in communication with a second cannula of the second bone fastener;
engaging the third mating element with the fourth mating element to connect the delivery device with the sleeve such that the lumen is in communication with the second channel;
inserting a second material into the lumen; and
inserting the plunger into the lumen such that the plunger moves the second material through the lumen and the second channel and into the second cannula.

17. The surgical method recited in claim 15, wherein the adapter has a first configuration and the second adapter has a second configuration, the second configuration being different than the first configuration.

18. The surgical method recited in claim 15, wherein the adapter has a first configuration and the second adapter has a second configuration, the second configuration being the same as the first configuration.

19. The surgical method recited in claim 15, wherein the bone fastener includes a saddle and engaging the first mating element with the second mating element comprises positioning a distal tip of the adapter through an aperture of the saddle and into a socket of the bone fastener such that the distal tip creates a seal with the saddle.

20. A surgical kit comprising:
bone cement;
a sleeve comprising a proximal end including a first mating element and a distal end including a second mating element, the sleeve defining a passageway;
a plurality of adapters, the adapters each being configured to be removably coupled to the sleeve, the adapters each defining a channel and comprising a distal portion and a proximal portion, the proximal portion being configured to be positioned in the passageway;
a delivery device comprising a handle and a shaft, a distal end of the shaft being configured to be positioned in a respective one of the channels, the handle comprising a third mating element configured to engage the first mating element to connect the delivery device to the sleeve, the shaft defining a lumen configured to be in communication with a respective one of the channels;
a plurality of bone fasteners, the bone fasteners each including a head and a shank defining a cannula, the heads each comprising a fourth mating element configured to engage the second mating element to connect the bone fasteners to the sleeve, a respective one of the distal portions being configured to be positioned in a respective one of the shanks such that a respective one of the channels is in communication with a respective one of the cannulas; and
a plunger configured to be movably disposed in the lumen and to move the bone cement through the lumen and a respective one of the channels and into a respective one of the cannulas.

* * * * *